United States Patent
Beauchamp et al.

(10) Patent No.: US 9,920,056 B2
(45) Date of Patent: Mar. 20, 2018

(54) 2-OXO-1,3,8-TRIAZASPIRO[4.5]DECAN-3-YL] CARBOXYLIC ACID DERIVATIVES

(71) Applicant: Eli Lilly and Company, Indianapolis, IN (US)

(72) Inventors: Thomas James Beauchamp, Fishers, IN (US); David Andrew Coates, New Palestine, IN (US); Maria Angeles Martinez-Grau, Madrid (ES); Miguel Angel Toledo, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/176,222

(22) Filed: Jun. 8, 2016

(65) Prior Publication Data
US 2016/0368922 A1    Dec. 22, 2016

(30) Foreign Application Priority Data

Jun. 16, 2015   (EP) ..................... 15382318
Nov. 20, 2015   (EP) ..................... 15382573

(51) Int. Cl.
*C07D 471/10* (2006.01)
(52) U.S. Cl.
CPC ................. *C07D 471/10* (2013.01)
(58) Field of Classification Search
None
See application file for complete search history.

(56) References Cited

U.S. PATENT DOCUMENTS

| | | |
|---|---|---|
| 6,482,829 B2 | 11/2002 | Galley et al. |
| 7,053,101 B2 | 5/2006 | Jordan et al. |
| 7,271,172 B2 | 9/2007 | Yang et al. |
| 7,754,744 B2 | 7/2010 | Binggeli et al. |
| 7,799,806 B2 | 9/2010 | Bleicher et al. |
| 7,968,568 B2 | 6/2011 | Christ et al. |
| 8,026,255 B2 | 9/2011 | Binggeli et al. |
| 8,026,365 B2 | 9/2011 | Christ et al. |
| 8,742,110 B2 | 6/2014 | Duffy et al. |
| 8,921,555 B2 | 12/2014 | Pierce et al. |
| 2010/0298342 A1 | 11/2010 | Egbertson et al. |
| 2012/0041012 A1 | 2/2012 | Aster et al. |
| 2013/0040978 A1 | 2/2013 | Duffy et al. |
| 2015/0099777 A1 | 4/2015 | Kasai et al. |
| 2016/0060273 A1 | 3/2016 | Kasai et al. |

FOREIGN PATENT DOCUMENTS

WO   WO 2010129729 A1 * 11/2010 ............ C07D 471/10
WO   WO 2012024183 A1 *  2/2012 ............ C07D 498/10

OTHER PUBLICATIONS

Wermuth, Camille. "Molecular Variations Based on Isoteric Replacements." The Practice of Medicinal Chemistry. Academic Press, 1996. pp. 203-237.*
Sprecher, U. et al., "Novel, non-petidic somatostatin receptor subtype 5 antagonists improve glucose tolerance in rodents", Regulatory Peptides, 2009, 19-27, 159.
Reutlinger, M. et al., "Neighborhood-Preserving Visualization of Adaptive Structure-Activity Landscapes: Application to Drug Discovery", Angewandte Chemie. Int. Ed., 2011, 11633-11636, 50.
Mehrotra, M. et al., "Discovery of Novel 2,8-Diazaspiro[4.5]decanes as Orally Active Glycoprotein IIb-IIIa Antagonists", J. Med. Chem., 2004, 2037-2061, 47.
Wang, X. et al., "The Effect of Global SSTR5 Gene Ablation on the Endocrine Pancreas and Glucose Regulation in Aging Mice 1", Journal of Surgical Research, 2004, 64-72, 129.
Hansen, L., "Somatostatin restrains the secretion of glucagon-like peptide-1 and -2 from isolated perfused porcine ileum", Am J Physiol Endoctrinol Metab, the American Physiological Society, E1010-E1018, 2000.

* cited by examiner

*Primary Examiner* — Deepak R Rao
*Assistant Examiner* — Laura M Daniel
(74) *Attorney, Agent, or Firm* — James B. Myers

(57) ABSTRACT

The present invention provides compounds of Formula 1,

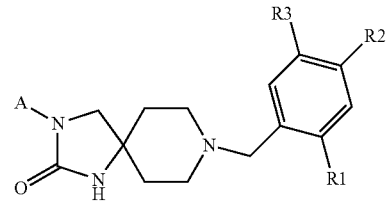

where A is selected from

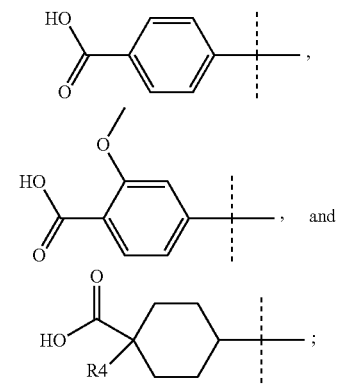

and R1, R2 and R3 are defined in the specification, or a pharmaceutically acceptable salt thereof, methods of using the compounds to treat diabetes, and processes for the synthesis of the compounds.

25 Claims, No Drawings

2-OXO-1,3,8-TRIAZASPIRO[4.5]DECAN-3-YL] CARBOXYLIC ACID DERIVATIVES

The present invention is directed to novel 2-oxo-1,3,8-triazaspiro[4.5]decan-3-yl]carboxylic acid derivatives, which are useful as somatostatin subtype receptor 5 antagonists and which may provide useful therapies for the treatment of diabetes including the modulation and control of blood glucose levels.

Diabetes is a condition, which is characterized by elevated blood glucose levels. Diabetes can be caused by a variety of pathological disorders. There are two main types of diabetic conditions, Type 1 insulin-dependent diabetes mellitus (IDDM) and Type 2, non-insulin dependent diabetes mellitus (NIDDM). Type 1 diabetes mellitus results from the failure of the beta cells to produce insulin or a sufficient amount of insulin for the body to absorb and utilize glucose. Type 2 diabetes mellitus is a multifactorial syndrome characterized by insulin resistance and often inadequate production of insulin; both conditions contribute to elevated blood glucose levels. Currently there are no known cures for diabetes. Patients being treated for Type 2 diabetes frequently advance from one medication and treatment regime to another as the patients become less proficient at producing insulin and become increasing insulin resistant. Eventually some Type 2 diabetic patients become Type 1 diabetics, which require insulin injections.

Consequently despite the advances in diabetic care there continues to be a need for alternative drugs and therapies for the treatment of diabetes. Alternative diabetic medications could provide additional treatment options and possibly forestall a patient's transition to Type 1 diabetes.

Somatostatin, a systemic hormone produced in the hypothalamus and secreted in various organs including the stomach, intestines and pancreas, inhibits secretion of insulin and glucagon by its interaction with the somatostatin receptors. Of the five known somatostatin receptors, somatostatin receptor 5 (SSTR5) is most directly associated with the regulation of insulin secretion and increased insulin sensitivity. For example, SSTR5 antagonists have been shown to decrease blood glucose levels in animals. Therefore it is thought that inhibiting somatostatin from binding to SSTR5 will decrease glucose levels and increase glucose sensitivity.

The present invention addresses one or more of these concerns and provides novel SSTR5 antagonists. In addition, the present invention provides novel SSTR5 antagonists, which may provide alternative treatment options for diabetic patients. Further the present invention may provide different medications that may act through a different mechanism of action than the current diabetic medications.

Published PCT application WO2010/129729 discloses spirocyclic amines, PCT application WO2011/146324 discloses spiroisoxazoline derivatives, and PCT application WO2012/024183 discloses spiroxazolidinone derivatives. These references note that certain of these derivatives are SSTR5 antagonists and may be useful for the treatment of diabetes.

The present invention provides a compound of the Formula 1:

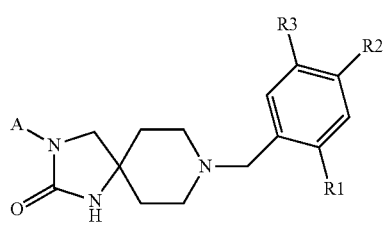

where A is selected from:

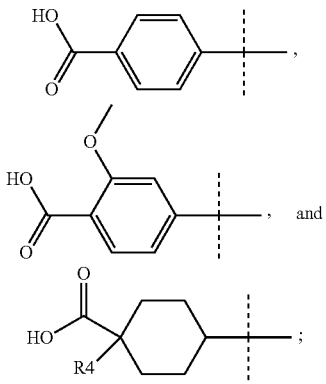

R1 is selected from: H, —$C_{1-3}$alkyl, F, Cl, —$OC_{1-2}$alkyl, and

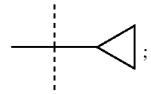

R2 is selected from: —$CH_3$, F, Cl, and —$OC_{1-2}$alkyl; R3 is selected from: —$C_{1-3}$alkyl, —$OC_{1-2}$alkyl, and

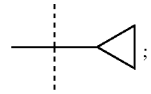

and R4 is —$C_{1-2}$alkyl; or a pharmaceutically acceptable salt thereof.

The present invention also provides a compound of Formula 1:

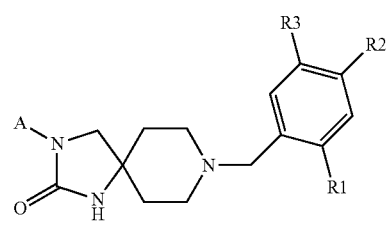

where A is selected from:

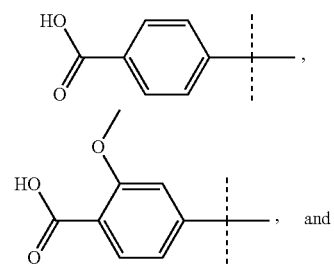

-continued

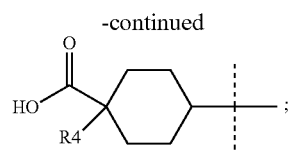

R1 is selected from: H, —C$_{1-3}$alkyl, F, Cl, —OC$_{1-2}$alkyl, and

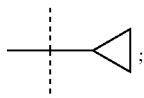

R2 is selected from: —CH$_3$, F, Cl, and —OC$_{1-2}$alkyl; R3 is selected from: —C$_{1-3}$alkyl, —OC$_{1-2}$alkyl, and

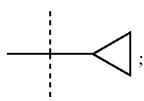

and R4 is —C$_{1-2}$alkyl.

In one form, the present invention provides a compound according to Formula 1 where A is

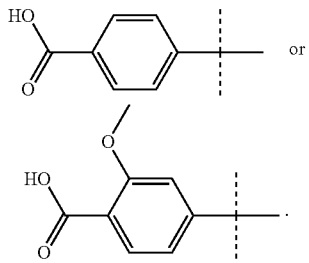

In another form, the present invention provides a compound according to Formula 1 where A is

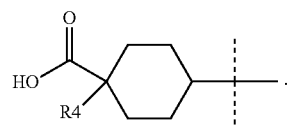

In another form, the present invention provides a compound according to Formula 1 where the carboxylic acid group and the 2-oxo-1,3,8-triazaspiro[4.5]decan-3-yl group on the cyclohexane ring are trans to each other, as illustrated below:

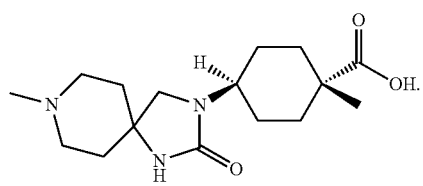 [SMILES: CN1CCC2(CC1)CN([C@H]1CC[C@](C)(C(=O)O)CC1)C(=O)N2]

In another form, the present invention provides a compound according to Formula 1, or a pharmaceutically acceptable salt thereof, where R1 is selected from: H, —C$_{1-3}$alkyl, F, Cl, —OC$_{1-2}$alkyl, and

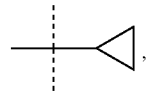

or a pharmaceutically acceptable salt thereof. In another form, R1 is —C$_{1-3}$alkyl or

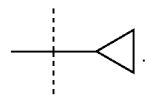

In yet another form, R1 is selected from: —CH$_2$CH$_3$, —CH$_2$CH$_2$CH$_3$, and

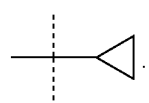

In still yet another form, R1 is F, or —OCH$_3$.

In another form, the present invention provides a compound according to Formula 1, or a pharmaceutically acceptable salt thereof, where R2 is Cl or —OCH$_3$. In yet another form, R2 is —CH$_3$.

In one form, the present invention provides a compound according to Formula 1, or a pharmaceutically acceptable salt thereof, where R3 is selected from: —C$_{1-3}$alkyl, —OC$_{1-2}$alkyl, and

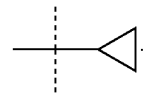

In another form, R3 is selected is —OC$_{1-2}$alkyl. In yet another form, R3 is —C$_{1-3}$alkyl, or

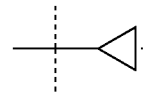

In another form, the present invention provides a compound according to Formula 1, or a pharmaceutically acceptable salt thereof, where R4 is —CH$_3$.

In one form, the present invention provides a compound according to Formula 1, or a pharmaceutically acceptable salt thereof, where R1 is selected from: —CH$_2$CH$_3$, —CH$_2$CH$_2$CH$_3$, and

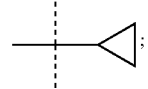

R2 is Cl or —OCH$_3$; R3 is selected from: —C$_{1-3}$alkyl, —OC$_{1-2}$alkyl, and

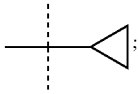

and R4 is —CH$_3$. In another form, R1 is selected from: —CH$_2$CH$_3$, —CH$_2$CH$_2$CH$_3$, and

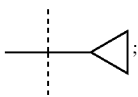

R2 is selected from: Cl, —CH$_3$; and —OCH$_3$; R3 is selected from: —C$_{2-3}$alkyl, —OC$_{1-2}$alkyl, and

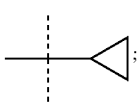

and R4 is —CH$_3$. In still yet another form, R1 is —C$_{1-3}$alkyl or

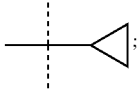

R2 is —CH$_3$; R3 is —OCH$_2$CH$_3$; and R4 is —CH$_3$.

In another embodiment, the present invention provides a compound of the Formula 2:

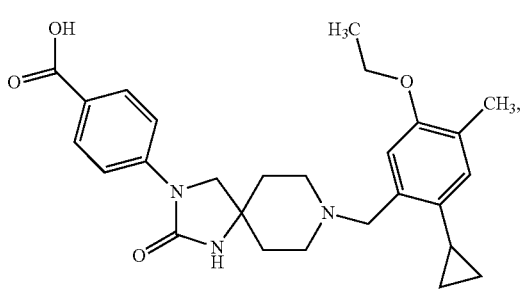

or a pharmaceutically acceptable salt thereof.

In another embodiment the present invention provides a compound of Formula 3

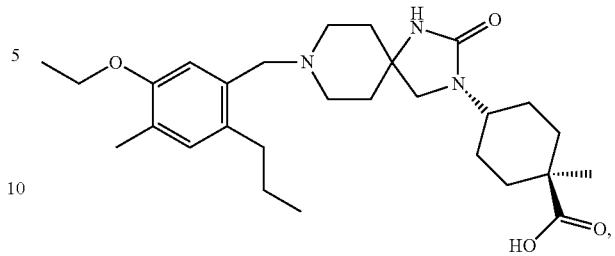

or a pharmaceutically acceptable salt thereof.

In yet another embodiment the present invention provides a compound of Formula 4

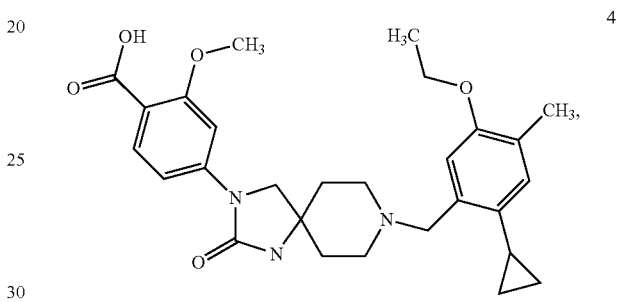

or a pharmaceutically acceptable salt thereof.

In one embodiment, a compound of any one of Formulae 1 to 4 is amphoteric and can exist as a zwitterion. In another embodiment, the compound is provided as a pharmaceutically acceptable salt. Since a compound of Formulae 1 to 4 is amphoteric, it can form either a base addition salt, such as a sodium salt by the addition of sodium hydroxide, or an acid addition salt, for example, by the addition of hydrogen chloride.

In one embodiment, the compound of Formulae 1 to 4 is provided as sodium 4-[8-[(2-cyclopropyl-5-ethoxy-4-methyl-phenyl)methyl]-2-oxo-1,3,8-triazaspiro[4.5]decan-3-yl]benzoate.

In another embodiment, the compound of Formula 1 is provided as 4-[8-[(2-cyclopropyl-5-ethoxy-4-methyl-phenyl)methyl]-2-oxo-1,3,8-triazaspiro[4.5]decan-3-yl]benzoic acid 2-tert-butyl amine.

In another embodiment, the compound of Formula 1 is provided as 4-[8-[(2-cyclopropyl-5-ethoxy-4-methyl-phenyl)methyl]-2-oxo-1,3,8-triazaspiro[4.5]decan-3-yl]benzoic acid hydrochloride.

In still yet embodiment, the present invention provides a compound of Formula 1 as a hydrate in 4-[8-[(2-cyclopropyl-5-ethoxy-4-methyl-phenyl)methyl]-2-oxo-1,3,8-triazaspiro[4.5]decan-3-yl]benzoic acid hydrate.

In still yet another embodiment, the present invention provides a compound of Formula 1 as sodium 4-[8-[(2-cyclopropyl-5-ethoxy-4-methyl-phenyl)methyl]-2-oxo-1,3,8-triazaspiro[4.5]decan-3-yl]benzoate in crystalline form characterized by an X-ray powder diffraction pattern obtained from a CuKα source (λ=1.54056 Å), which comprises peaks at: 4.4, 12.0, 15.6, and 19.6, +/−0.2° in 2 theta; or 4.4, 12.0, 15.6, 15.9, 19.6, and 22.0+/−0.2° in 2 theta; or 4.4, 8.1, 12.0, 15.6, 15.9, 19.6, 21.2, 22.0, and 25.6+/−0.2° in 2 theta.

In another form, the present invention provides a composition comprising substantially pure sodium 4-[8-[(2-cyclopropyl-5-ethoxy-4-methyl-phenyl)methyl]-2-oxo-1,3,8-triazaspiro[4.5]decan-3-yl]benzoate in crystalline form. Preferably the composition comprises greater than 80% (weight/weight) of sodium 4-[8-[(2-cyclopropyl-5-ethoxy-4-methyl-phenyl)methyl]-2-oxo-1,3,8-triazaspiro[4.5]decan-3-yl]benzoate in crystalline form. More preferably greater than 90% (weight/weight) of sodium 4-[8-[(2-cyclopropyl-5-ethoxy-4-methyl-phenyl)methyl]-2-oxo-1,3,8-triazaspiro[4.5]decan-3-yl]benzoate in crystalline form. Still more preferably greater than 95% (weight/weight) of sodium 4-[8-[(2-cyclopropyl-5-ethoxy-4-methyl-phenyl) methyl]-2-oxo-1,3,8-triazaspiro[4.5]decan-3-yl]benzoate in crystalline form.

In another form, the present invention provides a pharmaceutical composition comprising a compound according Formulae 1 to 4, a pharmaceutically acceptable salt thereof, and at least one of a pharmaceutically acceptable carrier, diluent, and/or excipient. In one embodiment the pharmaceutical composition comprises a compound of Formulae 1 to 4 as a neutral compound or zwitterion. In another embodiment the pharmaceutical composition comprises a compound of Formulae 1 to 4 as a pharmaceutically acceptable salt. In yet another embodiment, the pharmaceutical composition comprises a compound of Formulae 1 to 4 as a sodium salt or a tert-butylamine addition salt. In yet another embodiment, the pharmaceutical composition comprises 4-[8-[(2-cyclopropyl-5-ethoxy-4-methyl-phenyl)methyl]-2-oxo-1,3,8-triazaspiro[4.5]decan-3-yl]benzoic acid hydrate. In still yet another embodiment, the pharmaceutical composition comprises sodium 4-[8-[(2-cyclopropyl-5-ethoxy-4-methyl-phenyl)methyl]-2-oxo-1,3,8-triazaspiro[4.5]decan-3-yl]benzoate in crystalline form.

In yet another form, the present invention provides a method of treating a patient in need of treatment for diabetes. The method comprises administering to the patient an effective amount of a compound of Formulae 1 to 4, or a pharmaceutically acceptable salt thereof. In one preferred embodiment the method comprises treating a patient in need of treatment for Type 2 diabetes mellitus by administering a compound of Formulae 1 to 4, or a pharmaceutically acceptable salt thereof. In one embodiment the preferred method comprises administering an effective amount of a compound of Formulae 1 to 4 as a sodium salt or a tert-butylamine salt to treat Type 2 diabetes. In another embodiment the preferred method comprises administering an effective amount of 4-[8-[(2-cyclopropyl-5-ethoxy-4-methyl-phenyl)methyl]-2-oxo-1,3,8-triazaspiro[4.5]decan-3-yl]benzoic acid hydrate. In still yet another embodiment, the preferred method comprises administering an effective amount of sodium 4-[8-[(2-cyclopropyl-5-ethoxy-4-methyl-phenyl) methyl]-2-oxo-1,3,8-triazaspiro[4.5]decan-3-yl]benzoate in crystalline form.

In still yet another form, the present invention provides a method of treating a patient in need of treatment for diabetes. The method comprises administering to the patient an effective amount of a compound of Formulae 1 to 4, or a pharmaceutically acceptable salt thereof to modulate the patient's blood glucose level, more preferably to lower the patient's blood glucose level. In one embodiment, the method comprises administering to the patient an effective amount of 4-[8-[(2-cyclopropyl-5-ethoxy-4-methyl-phenyl) methyl]-2-oxo-1,3,8-triazaspiro[4.5]decan-3-yl]benzoic acid hydrate. In another embodiment, the method comprises an administering an effective amount of a compound of Formulae 1 to 4 as a sodium salt or a 2-methylpropan-2-amine salt. In still yet another embodiment, the pharmaceutical composition comprises sodium 4-[8-[(2-cyclopropyl-5-ethoxy-4-methyl-phenyl)methyl]-2-oxo-1,3,8-triazaspiro [4.5]decan-3-yl]benzoate in crystalline form.

In another form, the present invention provides a method of treating a patient in need of treatment for diabetes. The method comprises administering to the patient an effective amount of a pharmaceutical composition comprising a compound of Formulae 1 to 4 or a pharmaceutically salt and at least one of a pharmaceutically acceptable carrier, diluent, or excipient. Preferably the pharmaceutical composition is administered for the treatment of Type 2 diabetes mellitus. In one embodiment the pharmaceutical composition comprises an effective amount of 4-[8-[(2-cyclopropyl-5-ethoxy-4-methyl-phenyl)methyl]-2-oxo-1,3,8-triazaspiro [4.5]decan-3-yl]benzoic acid hydrate. In another embodiment, the pharmaceutical composition comprises an effective amount of a compound of Formulae 1 to 4 as a sodium salt or a 2-methylpropan-2-amine salt. In still yet another embodiment, the pharmaceutical composition comprises sodium 4-[8-[(2-cyclopropyl-5-ethoxy-4-methyl-phenyl)methyl]-2-oxo-1,3,8-triazaspiro[4.5]decan-3-yl]benzoate in crystalline form.

The present invention also provides a compound of Formulae 1 to 4, or a pharmaceutically acceptable salt thereof, for use in therapy. Preferably the therapy is for the treatment of diabetes. More preferably the therapy is for the treatment of Type 2 diabetes mellitus. In one embodiment, the compound for use in therapy is 4-[8-[(2-cyclopropyl-5-ethoxy-4-methyl-phenyl)methyl]-2-oxo-1,3,8-triazaspiro[4.5]decan-3-yl]benzoic acid hydrate. In another embodiment the compound for use in therapy is a compound of Formulae 1 to 4 as a sodium salt or a tert-butyl amine salt. In another embodiment the compound for use in therapy is sodium 4-[8-[(2-cyclopropyl-5-ethoxy-4-methyl-phenyl)methyl]-2-oxo-1,3,8-triazaspiro[4.5]decan-3-yl]benzoate in crystalline form.

The present invention also provides use of a compound according to Formulae 1 to 4, or a pharmaceutically acceptable salt thereof, in the manufacture of a medicament to treat diabetes, preferably to treat Type 2 diabetes mellitus. In one embodiment, the compound for the manufacture of a medicament is 4-[8-[(2-cyclopropyl-5-ethoxy-4-methyl-phenyl) methyl]-2-oxo-1,3,8-triazaspiro[4.5]decan-3-yl]benzoic acid hydrate. In another embodiment the compound for the manufacture of a medicament is a compound of Formulae 1 to 4 as a sodium salt or a tert-butylamine salt. In still yet another embodiment the compound of the manufacture of a medicament is sodium 4-[8-[(2-cyclopropyl-5-ethoxy-4-methyl-phenyl)methyl]-2-oxo-1,3,8-triazaspiro[4.5]decan-3-yl]benzoate in crystalline form.

The present invention also provides a compound of the present invention for use in simultaneous, separate or sequential combination with one or more additional therapeutic agents. Preferably the present invention provides a compound according to Formulae 1 to 4, or a pharmaceutically acceptable salt thereof; in combination with one or more additional therapeutic agents. Preferably the additional therapeutic agents are agents useful for treating diabetes. In one embodiment, the compound is 4-[8-[(2-cyclopropyl-5-ethoxy-4-methyl-phenyl)methyl]-2-oxo-1,3,8-triazaspiro [4.5]decan-3-yl]benzoic acid hydrate. In another embodiment, the compound is a sodium salt or a tert-butyl amine salt. In still yet another embodiment, the compound is sodium 4-[8-[(2-cyclopropyl-5-ethoxy-4-methyl-phenyl) methyl]-2-oxo-1,3,8-triazaspiro[4.5]decan-3-yl]benzoate in crystalline form.

The present invention further provides a compound of Formulae 1 to 4, or a pharmaceutically acceptable salt thereof for use in simultaneous, separate or sequential combination with additional therapeutic agents in the treatment of diabetes. In one embodiment, the compound is 4-[8-[(2-cyclopropyl-5-ethoxy-4-methyl-phenyl)methyl]-2-oxo-1,3,8-triazaspiro[4.5]decan-3-yl]benzoic acid hydrate. In another embodiment, the compound of Formulae 1 to 4 is a sodium salt or a 2-methylpropan-2-amine salt. In still yet another embodiment, the compound is sodium 4-[8-[(2-cyclopropyl-5-ethoxy-4-methyl-phenyl)methyl]-2-oxo-1,3,8-triazaspiro[4.5]decan-3-yl]benzoate in crystalline form.

Non-limiting examples of the additional therapeutic agents that can be combined with the compound of the present invention in the embodiments mentioned above include: insulin; biguanides, such as metformin; sulfonylureas (SU) such as glimepiride, glipizide, and glyburide; thiazolidinediones (TZD) such as pioglitazone; dipeptidyl peptidase-4 (DPP-4) inhibitors such as sitagliptin, saxagliptin, and alogliptin; sodium-dependent glucose transporter (SGLT2) inhibitors such as dapaglifozin, and canaglifozin; and glucagon-like-peptide-1 (GLP-1) analogs.

The exemplified compounds and the additional therapeutic agent(s) can be administered either together through the same delivery route and device such as a single pill, capsule or tablet; or separately administered either at the same time in separate delivery devices or administered sequentially.

The present invention also provides a process for the preparation of a compound of Formula 1, or a pharmaceutically acceptable salt thereof. The process comprises deprotecting a compound according to Formula 5:

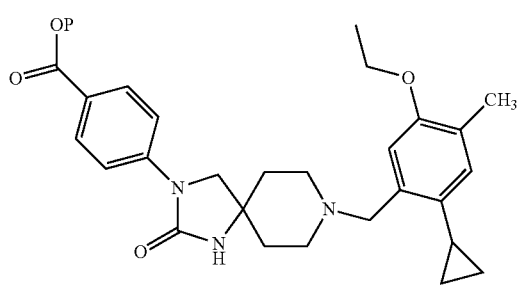

5 wherein P is a protecting group for a carboxylic acid functionality, which can be removed, to provide a compound of Formula 1 or 2.

In one embodiment the process also includes coupling a compound of Formula 6

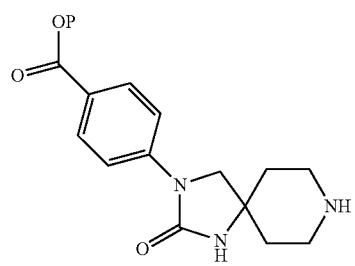

6 with a compound of Formula 7 under conditions to provide a compound of Formula 5

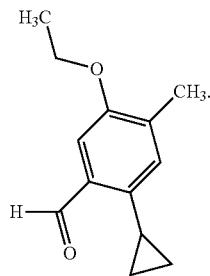

7

Examples of various acid protecting functionalities, methods of preparing the protected acids, and methods for deprotecting the acids can be found in "Greene's Protective Groups in Organic Synthesis", 5th Ed., Wuts, P. G. M., Eds. John Wiley and Sons, 2014. It will be recognized by those skilled in the art that in addition to the carboxylic acid and protected carboxylic acid other functional groups that can be readily converted to a carboxylic acid can be used in place of the carboxylic acid or protected acid. Such functional groups, preparations, and transformations of these groups to carboxylic acids can be found in "Comprehensive Organic Transformations: A Guide to Functional Group Preparations" by Larock. R. C, Wiley VCH, 1999 and in "March's Advanced Organic Chemistry: Reactions, Mechanisms and Structure" Smith, M. B., Wiley-Interscience, 7th Ed., 2013.

The term "pharmaceutically-acceptable salt" as used herein refers to a salt of a compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, 2nd Revised Edition, Wiley-VCH, 2011; S. M. Berge, et al., "Pharmaceutical Salts," *Journal of Pharmaceutical Sciences*, Vol. 66, No. 1, January 1977.

The pharmaceutical composition for the present invention may be prepared by procedures known in the art using one or more pharmaceutically acceptable additives. The term "pharmaceutically acceptable additive(s)" as used herein are those carriers, diluents, and excipients that are compatible with the other ingredients of the formulation and not deleterious to the patient. Typically, the pharmaceutically acceptable carriers, diluents, and excipients are approved by a regulatory agency such as the Food and Drug Agency or the European Medicines Agency and/or generally recognized as safe. Pharmaceutical compositions and processes for their preparation are known in the art and examples can be found in "Remington: The Science and Practice of Pharmacy" (A. Gennaro, et al. eds. 21$^{st}$ Ed., Mack Publishing Co., 2005). Non-limiting examples of pharmaceutically acceptable carriers, diluents, and excipients include the following: starch, sugars, mannitol, and silica derivatives; binding agents such as carboxymethyl cellulose and other cellulose derivatives, alginates, gelatin, and polyvinyl-pyrrolidone; kaolin and bentonite; polyethyl glycols.

The expression —$C_{1-3}$alkyl as used herein refers to straight chained alkyl; for example —$CH_3$, —$CH_2CH_3$, or —$CH_2CH_2CH_3$; or a branched chain alkyl; for example —$CH(CH_3)_2$.

As used herein a bond bisected with a dashed line as in the following symbol

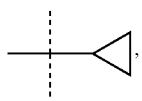

indicates the bond that attaches the group, in this example the cyclopropyl group, to the other portion of the molecule.

As used herein, the term "effective amount" of a compound of Formula 1 or 2 refers to an amount that is a dosage, which is effective in treating a disorder, such as diabetes or Type 2 diabetes mellitus. In one form, the effective amount is the amount of a compound of Formula 1 or 2, a pharmaceutically acceptable salt thereof, or a hydrate of the compound of Formula 1 or 2 that will modulate a patient's blood glucose level, more preferably lower a patient's blood glucose level. An attending diagnostician can readily determine an effective amount by the use of conventional techniques and by observing results obtained under analogous circumstances. In determining an effective amount of a compound of Formula 1 or 2, or its pharmaceutically acceptable salt, a number of factors are considered, including, but not limited to whether a compound of Formula 1 or 2, or a pharmaceutically accept salt thereof, will be administered; the co-administration of other agents, if used; the species of mammal; its size, age, and general health; the degree of involvement or the severity of the disorder; the response of the individual patient; the mode of administration; the bioavailability characteristics of the preparation administered; the dose regimen selected; the use of other concomitant medication; and other relevant circumstances.

As used herein, the terms "treating", "to treat", or "treatment", includes restraining, slowing, stopping, reducing, or reversing the progression or severity of an existing symptom, disorder, condition, such as an elevated blood glucose level or hyperglycemia, improve glycemic control, and attendant complications that can result from diabetes.

As used herein, patient refers to an animal in need of treatment, preferably not exclusively a mammal, preferably a human; or alternatively a companion animal, such as a dog or cat or a domesticated animal, such as, a cow, pig, sheep, goat and horse.

A treating physician, veterinarian, or other medical person will be able to determine an effective amount of the compound for treatment of a patient in need. Preferred pharmaceutical compositions can be formulated as a tablet or capsule for oral administration. The tablet or capsule can include a compound of the present invention in an amount effective for treating a patient in need of treatment for diabetes, preferably Type 2 diabetes mellitus.

Chemistry Section

As used herein, the following terms have the meanings indicated: "BSA" refers to Bovine Serum Albumin; "CRC" refers to concentration response curve; "DCM" refers to dichloromethane; "DMEA" refers to dimethylethylamine; "DMSO" refers to dimethylsulfoxide; "DPP4" refers to dipeptidyl peptidase 4; "EDTA" refers to ethylenediaminetetraacetic acid; "EtOAc" refers to ethyl acetate; "ES/MS" refers to electrospray ionization mass spectroscopy; "EtOH" refers to ethanol; "GPCR" refers to G-protein couple receptor; "HBSS" refers to Hank's balanced salt solution; "HEC" refers to hydroxyethylcellulose; "HEPES" refers to 4-(2-hydroxyethyl)piperazine-1-ethanesulfonic acid; "HLB" refers to Hydrophilic-Lipophilic-Balanced; "hr" or "hrs" refers to hour or hours, respectively; "IC$_{50}$" refers to the concentration of an agent that produces 50% of the maximal inhibitory response possible for that agent; "MeOH" refers to methanol; "min" refers to minutes; "MS" refers to mass spectroscopy; "MTBE" refers to methyl tert-butyl ether; "PBS" refers to phosphate buffered saline; "Prep No." refers to Preparation Number; "RP-HPLC" refers to reverse phase high performance liquid chromatography; "rpm" refers to revolutions per minute; "rt" or "RT" refers to room temperature; SCX refers to strong cation exchange; "THF" refers to tetrahydrofuran; "Ex. No." refers to Example Number.

The compounds of the present invention, or salts thereof, may be prepared by a variety of procedures known in the art, some of which are illustrated in the Preparations and Examples below. The products of each procedure can be isolated by conventional methods well known in the art, including extraction, evaporation, precipitation, chromatography, filtration, trituration, and crystallization. The reagents and starting materials are readily available to one of ordinary skill in the art unless noted below.

PREPARATION 1 tert-Butyl 2-oxo-1,3,8-triazaspiro[4.5]decane-8-carboxylate

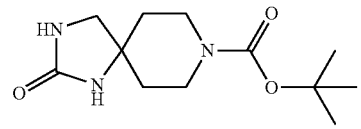 [SMILES: CC(C)(C)OC(=O)N1CCC2(CC1)CNC(=O)N2]

Add 1,1'-carbonyldiimidazole (15.4 g, 93.3 mmol) to a solution of tert-butyl 4-amino-4-(aminomethyl)piperidine-1-carboxylate (21.4 g, 93.3 mmol) in DCM (1.10 L) and stir the resulting mixture at rt overnight. Add water (0.5 L) then stir the resulting mixture for 30 min Separate the two phases, dry the organic phase over MgSO$_4$, filter, and concentrate the filtrate under reduced pressure to afford the title compound (23.16 g, 97% yield). ES/MS m/z 256 (M+H).

PREPARATION 2 tert-Butyl 3-(4-tert-butoxycarbonylphenyl)-2-oxo-1,3,8-triazaspiro[4.5]decane-8-carboxylate

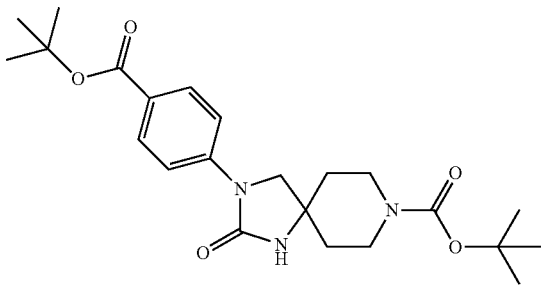 [SMILES: CC(C)(C)OC(=O)c1ccc(N2CC3(CCN(C(=O)OC(C)(C)C)CC3)NC2=O)cc1]

Combine tert-butyl 2-oxo-1,3,8-triazaspiro[4.5]decane-8-carboxylate (10 g, 39.16 mmol), CuI (1.5 g, 7.9 mmol), trans-N,N'-dimethylcyclohexane-1,2-diamine (2.3 g, 16 mmol), tert-butyl 4-bromobenzoate (11.3 g, 43.1 mmol), and powdered potassium carbonate (11 g, 79.59 mmol) in toluene (100 mL). Heat the mixture to reflux and stir for 20 hrs under a nitrogen atmosphere. Cool the mixture to rt, dilute it with chloroform (200 mL), filter it through a pad of diatomaceous earth, and rinse with chloroform (2×100 mL). Collect the dark filtrate and sequentially wash the filtrate with water (2×500 mL) and brine (500 mL). Combine the aqueous rinses and extract with chloroform (500 mL). Combine all the organic layers and dry over MgSO$_4$, filter, collect the filtrate, and concentrate the filtrate under reduced pressure to provide a solid. Dissolve the solid in EtOAc (2.5 L), and concentrate the mixture under reduced pressure to induce a suspension. Add hexanes (2 L) to the suspension, and stir the resulting thick slurry at rt for 2 hrs. Collect the resulting solid by filtration, wash the solid with hexanes, and dry in a vacuum oven at 55° C. to afford the title compound as a white solid (14.4 g, 84% yield). ES/MS m/z 432 (M+H).

PREPARATION 3 tert-Butyl 3-(4-methoxycarbonylphenyl)-2-oxo-1,3,8-triazaspiro[4.5]decane-8-carboxylate

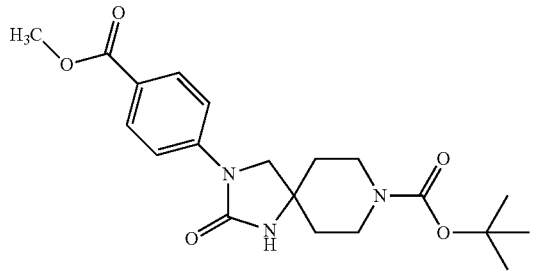 [SMILES: COC(=O)c1ccc(N2CC3(CCN(C(=O)OC(C)(C)C)CC3)NC2=O)cc1]

Suspend methyl 4-bromobenzoate (506 g, 2353 mmol) and tert-butyl 2-oxo-1,3,8-triazaspiro[4.5]decane-8-carboxylate (600 g, 2350 mmol) in toluene (12 L). Add potassium carbonate (650 g, 4703 mmol), CuI (90 g, 472.56 mmol) and trans-N,N'-dimethylcyclohexane-1,2-diamine (138 g, 941 mmol). Stir the resulting blue slurry at rt for 10 min, then raise the internal temperature to 100° C. while stirring for 21 hrs (99% conversion). Cool the mixture to 15° C. over a period of 60 min; filter to collect the solid; and rinse the solid with toluene (3 L). Suspend the resulting light blue solid in water (8.0 L). (Observe an exotherm from 23° C. to 27° C.). Stir the suspension for 2 hrs and cool the suspension to 23° C. Filter to collect the solid and rinse the solid with water (5 L). Re-suspend the light blue solid as well as 116 g of a previous crude lot of tert-butyl 3-(4-methoxycarbonylphenyl)-2-oxo-1,3,8-triazaspiro[4.5]decane-8-carboxylatein water (2.5 L). Add aqueous NH₄OH (23%, 800 mL). Stir the slurry for 12 hrs at 23° C. Filter the suspension to collect the solid; rinse the solid with water (5 L); and dry under a slight vacuum under a N₂ atmosphere to a constant weight to provide the title compound as an off-white solid (775 g, 84% yield). ES/MS m/z 390.2 (M+H).

PREPARATION 4 tert-Butyl 4-(2-oxo-1,3,8-triazaspiro[4.5]decan-3-yl)benzoate hydrochloride

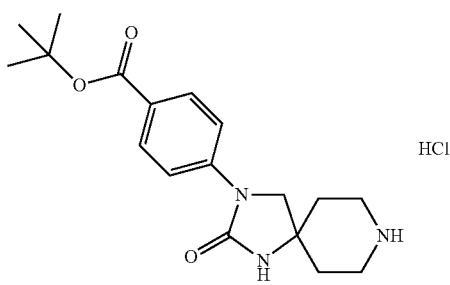 [SMILES: CC(C)(C)OC(=O)c1ccc(N2CC3(CCNCC3)NC2=O)cc1 ; Cl]

Suspend tert-butyl 3-(4-tert-butoxycarbonylphenyl)-2-oxo-1,3,8-triazaspiro[4.5]decane-8-carboxylate (56.6 g, 131 mmol) in isopropanol (1.4 L). Warm the slurry to 70° C., and drop-wise add a 1.1 M anhydrous solution of HCl in isopropanol (310 mL), prepared by adding acetyl chloride in a controlled fashion to isopropanol. Stir the mixture at 70° C. for two hrs and allow the slurry to slowly cool to 24° C. Isolate the solid by filtration and dry overnight at 60° C. in a vacuum oven to afford the title compound as a white solid (46.2 g, 81% yield). ES/MS m/z 332 (M+H).

PREPARATION 5 tert-Butyl 3-(3-methoxy-4-methoxycarbonyl-phenyl)-2-oxo-1,3,8-triazaspiro[4.5]decane-8-carboxylate

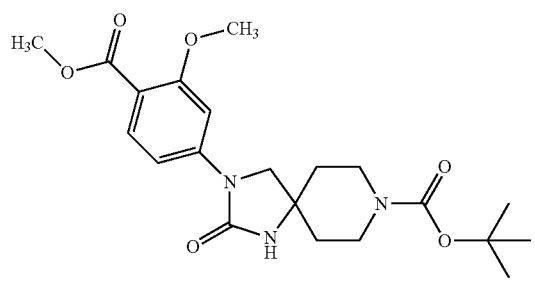 [SMILES: COC(=O)c1ccc(N2CC3(CCN(C(=O)OC(C)(C)C)CC3)NC2=O)cc1OC]

Prepare the title compound essentially by the method of Preparation 3 in 75% yield starting from methyl 4-bromo-2-methoxy-benzoate and tert-butyl 2-oxo-1,3,8-triazaspiro[4.5]decane-8-carboxylate. ES/MS m/z 420.2 (M+H).

PREPARATION 6

Methyl 4-(2-oxo-1,3,8-triazaspiro[4.5]decan-3-yl)benzoate hydrochloride

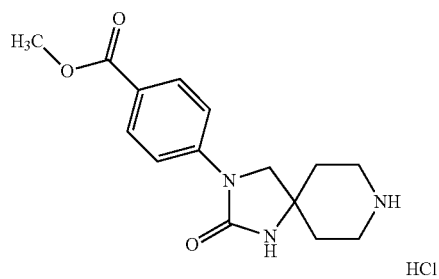 [SMILES: COC(=O)c1ccc(N2CC3(CCNCC3)NC2=O)cc1 ; Cl]

Suspend tert-butyl 3-(4-methoxycarbonylphenyl)-2-oxo-1,3,8-triazaspiro[4.5]decane-8-carboxylate (300 g, 770.4 mmol) in DCM (4.0 L) and add 4M HCl in 1,4-dioxane over 4.5 hr (92% conversion), using an in-process control (HPLC) to ensure dose controlled addition. Stir the suspension for 18 hrs to achieve 100% conversion. Dilute the suspension with MTBE (6.0 L), stir for 1 hr at 23° C.; filter; then rinse the solid with MTBE (3.0 L). Collect and dry the solid at 23° C. under vacuum with a N₂ bleed (nitrogen press) to provide the title compound as a white solid (251.0 g, 100% yield). ES/MS m/z 290 (M+H).

PREPARATION 7

Methyl 2-methoxy-4-(2-oxo-1,3,8-triazaspiro[4.5]decan-3-yl)benzoate hydrochloride

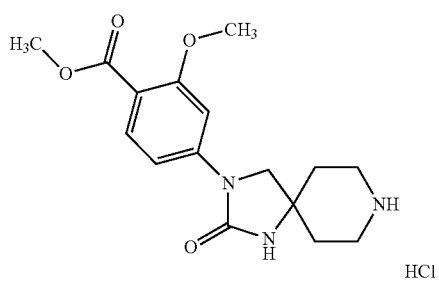 [SMILES: COC(=O)c1ccc(N2CC3(CCNCC3)NC2=O)cc1OC ; Cl]

Prepare the title compound essentially by the method of Preparation 6 in 90% yield starting from tert-butyl 3-(3-methoxy-4-methoxycarbonyl-phenyl)-2-oxo-1,3,8-triazaspiro[4.5]decane-8-carboxylate. ES/MS m/z 320.2 (M+H).

PREPARATION 8 tert-Butyl 4-amino-4-[[(4-ethoxycarbonyl-4-methyl-cyclohexyl)amino]methyl]piperidine-1-carboxylate

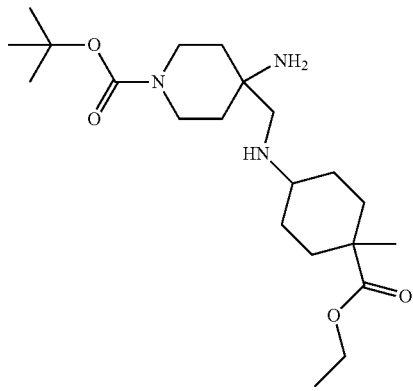 [SMILES: CCOC(=O)C1(C)CCC(NCC2(N)CCN(C(=O)OC(C)(C)C)CC2)CC1]

Add sodium triacetoxyborohydride (71.4 g, 336.9 mmol) to a mixture of tert-butyl 4-amino-4-(aminomethyl)piperidine-1-carboxylate acetic acid salt (75 g, 259.2 mmol), ethyl 1-methyl-4-oxo-cyclohexanecarboxylate (57.29 g, 311.0 mmol) and acetic acid (14.85 mL, 259.2 mmol) in DCM (259 mL) at rt. After 16 hrs, dilute the mixture with DCM and saturated aqueous NaHCO$_3$. Separate the resulting layers and back extract the aqueous phase with DCM. Wash the combined organic layers with saturated aqueous NaHCO$_3$ and brine; then dry over sodium sulfate. Filter the mixture and concentrate the filtrate under reduced pressure. Subject the residue to column chromatography to give the title compounds as a yellow oil (133 g, 75% yield as a 60/40 mixture of cis/trans isomers). ES/MS m/z 398 (M+H).

PREPARATION 9 tert-Butyl 3-(4-ethoxycarbonyl-4-methyl-cyclohexyl)-2-oxo-1,3,8-triazaspiro[4.5]decane-8-carboxylate

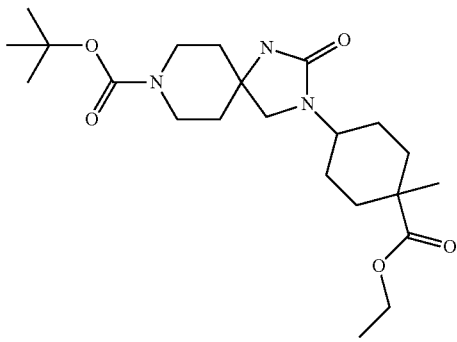 [SMILES: CCOC(=O)C1(C)CCC(N2CC3(CCN(C(=O)OC(C)(C)C)CC3)NC2=O)CC1]

Add 1,1'-carbonyldiimidazole (77.29 g, 476.7 mmol) portion-wise to a stirred solution of tert-butyl 4-amino-4-[[(4-ethoxycarbonyl-4-methyl-cyclohexyl)amino]methyl]piperidine-1-carboxylate (133 g, 190.7 mmol, 60/40 mixture of cis/trans isomers) in DCM (572 mL). Stir the resulting mixture at rt for 3 hours. Dilute the mixture with DCM and water at rt. Caution; gas evolves during the water addition. Separate the organic layer and dry over Na$_2$SO$_4$; filter, and remove the solvent from the filtrate under reduced pressure to provide a residue. Absorb the residue on silica gel and subject it to flash chromatography eluting with a gradient of hexane/acetone (from 10 to 60% of acetone). Concentrate the desired fractions under reduced pressure to give the title compound as a white solid (45 g, 52% yield, 60/40 mixture of cis/trans isomers). ES/MS m/z 424 (M+H).

PREPARATION 10

Ethyl 1-methyl-4-(2-oxo-1,3,8-triazaspiro[4.5]decan-3-yl)cyclohexanecarboxylate hydrochloride Prepare the title compound essentially by the method of Preparation 6 in 74% yield (60/40 mixture of cis/trans isomers) starting from tert-butyl 3-(4-ethoxycarbonyl-4-methyl-cyclohexyl)-2-oxo-1,3,8-triazaspiro[4.5]decane-8-carboxylate (60/40 mixture of cis/trans isomers). ES/MS m/z 324.2 (M+H).

PREPARATION 11

Ethyl 1-methyl-4-(2-oxo-1,3,8-triazaspiro[4.5]decan-3-yl)cyclohexanecarboxylate

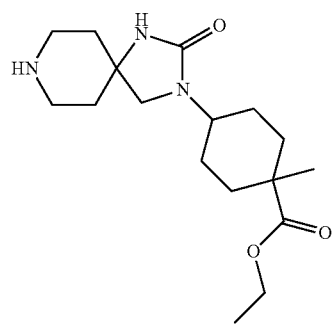 [SMILES: CCOC(=O)C1(C)CCC(N2CC3(CCNCC3)NC2=O)CC1]

Add 4M HCl in 1,4-dioxane (40 mL) to a stirred solution of tert-butyl 3-(4-ethoxycarbonyl-4-methyl-cyclohexyl)-2-oxo-1,3,8-triazaspiro[4.5]decane-8-carboxylate (8.5 g, 16 mmol, 60/40 mixture of cis/trans isomers) in DCM (80 mL). Stir the mixture at rt for 2 hrs. Remove the solvent to provide the crude material. Subject the crude material to a SCX cartridge (50 g, Biotage) eluting twice with MeOH and then twice with 2N ammonia in MeOH. Collect the basic fractions and remove the volatiles to give the title compound as pale yellow solid (63% yield, 60/40 mixture of cis/trans isomers). ES/MS m/z 324 (M+H).

PREPARATION 12 tert-Butyl 4-cyano-4-(ethoxycarbonylamino)piperidine-1-carboxylate

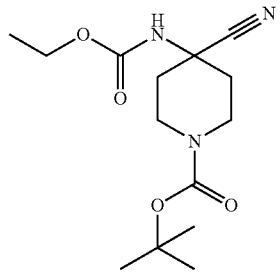 [SMILES: CCOC(=O)NC1(C#N)CCN(C(=O)OC(C)(C)C)CC1]

Add N,N-diisopropylethylamine (143 mL, 820 mmol) and ethyl chloroformate (81 mL, 847.1 mmol) to a solution of tert-butyl 4-amino-4-cyano-piperidine-1-carboxylate (92 g, 408.36 mmol) in THF (1 L). The reaction is exothermic and the internal temperature rises to 45° C., but gradually returns to rt. Stir the mixture at rt for 1 hr. Dilute the mixture with water (2 L) and DCM (2 L); mix the resulting layers. Separate the layers. Wash the organic layer with 10% aqueous citric acid (2 L) followed by brine (1 L). Dry the organic layer over Na$_2$SO$_4$; filter, and concentrate the filtrate to provide an oil. Stir the oil in hexanes (1500 mL); seed with solid tert-butyl-4-cyano-4-(ethoxycarbonylamino)piperidine-1-carboxylate, and stir at rt for 1 hr. Filter to collect the resulting solid and rinse the solid with hexanes (150 mL). Dry the solid under vacuum at 55° C. to give the title compound as a light beige solid (118.7 g, 98% yield). $^1$H NMR (400 MHz, CDCl$_3$) δ 4.95 (bs, 1H), 4.17 (q, 2H), 3.92 (m, 2H), 3.24 (m, 2H), 2.34 (m, 2H), 1.75 (m, 2H), 1.44 (s, 9H), 1.26 (t, 3H).

PREPARATION 13 tert-Butyl 4-(aminomethyl)-4-(ethoxycarbonylamino)piperidine-1-carboxylate

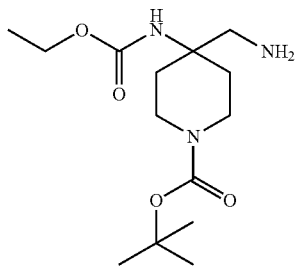 [SMILES: CCOC(=O)NC1(CN)CCN(C(=O)OC(C)(C)C)CC1]

Add a solution of tert-butyl 4-cyano-4-(ethoxycarbonylamino)piperidine-1-carboxylate (59.3 g, 199 mmol) in 2M ammonia in EtOH (460 mL) to a mixture of Raney-Nickel catalyst (10 g) in 2M ammonia in EtOH (200 mL). Exchange the nitrogen atmosphere in the reaction vessel with hydrogen. Then pressurize the vessel with hydrogen gas (60 psi), heat to 60° C. and shake for 18 hrs. Filter the mixture under nitrogen through diatomaceous earth to give a milky, off-white filtrate. Repeat the reduction on an additional amount of tert-butyl 4-cyano-4-(ethoxycarbonylamino)piperidine-1-carboxylate (59.3 g). Combine the two milky, off-white filtrates and concentrate under reduced pressure to give the title compound as an oil (114.8 g, 91% yield). ES/MS m/z 302 (M+H).

PREPARATION 14 tert-Butyl trans-4-(ethoxycarbonylamino)-4-[[(4-ethoxycarbonyl-4-methylcyclohexyl)amino]methyl]piperidine-1-carboxylate

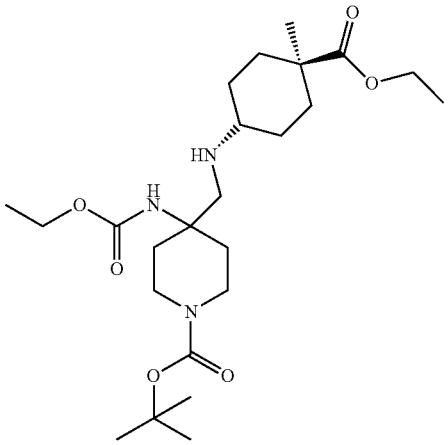

Add ethyl 1-methyl-4-oxo-cyclohexanecarboxylate (41 g, 222 mmol) to a solution of tert-butyl 4-(aminomethyl)-4-(ethoxycarbonylamino)piperidine-1-carboxylate (67 g, 222 mmol) in EtOH (670 mL). Stir the mixture for 1 hr; then add a 5:2 mixture of formic acid:trimethylamine complex, respectively (120 mL, 281.4 mmol) at 22° C. The reaction is exothermic (3° C. exotherm). Stir the mixture for 20 min; then add a suspension of dichloro(pentamethylcyclopentadienyl)iridium (III) dimer (0.93 g, 1.1 mmol) and (1S,2S)-(+)-N-(4-toluenesulfonyl)-1,2-diphenylethylenediamine (1.25 g, 3.34 mmol) in EtOH (67 mL) over 10 min. The reaction is exothermic (4° C. exotherm) and may effervesce. The resulting amber solution turns dark orange over 20 min; LC-MS analysis indicates a high conversion. Concentrate the mixture under reduced pressure at 40° C. to provide a residue. Dissolve the residue in DCM (500 mL); then slowly adjust the pH to 8.0 by adding an aqueous saturated solution of sodium bicarbonate. Separate the resulting layers. Dry the organic layer over Na$_2$SO$_4$; filter, and concentrate the filtrate to give the title compound as an amber oil (96.7 g, 83% yield as a 9:1 mixture of trans/cis isomers). ES/MS m/z 470 (M+H).

PREPARATION 15a

Sodium trans-4-(8-tert-butoxycarbonyl-2-oxo-1,3,8-triazaspiro[4.5]decan-3-yl)-1-methyl-cyclohexanecarboxylate

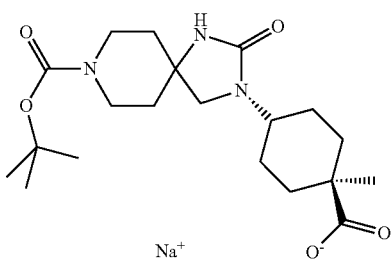

Add aqueous NaOH (30 w/w %, 7.5 mL, 75 mmol) to a solution of tert-butyl 4-(ethoxycarbonylamino)-4-[[(4-ethoxycarbonyl-4-methyl-cyclohexyl)amino]methyl]piperidine-1-carboxylate (17.2 g, 33.0 mmol, 9:1 trans:cis ratio) in EtOH (75 mL). Heat the resulting heterogeneous mixture to 65° C. for 4 hrs; then add an additional amount of aqueous NaOH (30 w/w %, 7.5 mL, 75 mmol). Stir for 12 hrs; then add aqueous NaOH (30 w/w %, 7.5 mL, 75 mmol) and EtOH (75 mL). Stir at 65° C. for 4 hrs. Cool the mixture to 24° C., concentrate in vacuo to half its original volume and filter to give the title compound as a white solid (7.74 g, 56% yield). The ratio of trans to cis is 99.5 to 0.5, respectively, as measured by HPLC at 300 nm (LC-MS method: 2×50 Xbridge C18 3.5 um column; 5-95% B gradient in 1.5 minutes with a 0.25 minute hold at 95% B; A: 10 mM (NH$_4$)HCO$_3$ in water pH=9, B:Acetonitrile; Flow Rate=1.2 mL/min; Column Temp=50 degrees; cis isomer retention time=0.62 min; trans isomer retention time=0.71 min) ES/MS m/z 396.2 (M+H).

PREPARATION 15b trans-4-(8-tert-Butoxycarbonyl-2-oxo-1,3,8-triazaspiro[4.5]decan-3-yl)-1-methyl-cyclohexanecarboxylic acid

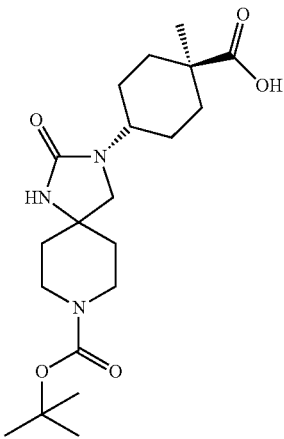

Add aqueous NaOH (80 mL, 30 w/w %, 800 mmol) to a solution of tert-butyl trans-4-(ethoxycarbonylamino)-4-[[(4-ethoxycarbonyl-4-methyl-cyclohexyl)amino]methyl]piperidine-1-carboxylate (92 g, 195.9 mmol, 9:1 mixture of trans:cis isomers) in EtOH (800 mL) at 22° C. Heat the mixture to 75° C. overnight. Add aqueous NaOH (20 mL, 30 wt/wt %, 200 mmol) to this mixture. Heat the mixture to 75° C. for 45 min. Cool the resulting slurry and concentrate in vacuo (external temp bath at 40° C.). Suspend the resulting semi-solid in DCM (350 mL) and cool to 5° C. Adjust the pH of the solution to 1.4 with aqueous 5N aqueous HCl. Add brine to break up any emulsion that forms. Separate the layers. Extract the aqueous layer with EtOAc (250 mL). Dry the combined organic layers over Na$_2$SO$_4$; filter, and concentrate the filtrate in vacuo to give an amber solid. Triturate the solid with MTBE (600 mL). Filter and dry the solid to give the title compound as an off-white solid (41 g, 48% yield; ca. 96:4 mixture of trans1 cis isomers). ES/MS m/z 396 (M+H).

PREPARATION 16

Ethyl trans-1-methyl-4-(2-oxo-1,3,8-triazaspiro[4.5]decan-3-yl) cyclohexanecarboxylate hydrochloride

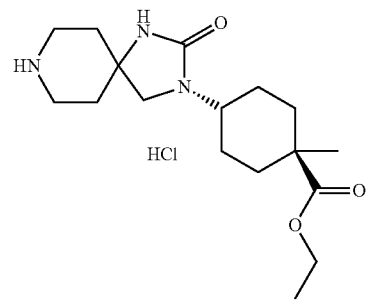

Add acetyl chloride (20 mL, 278 mmol) drop-wise to a slurry of 4-(8-tert-butoxycarbonyl-2-oxo-1,3,8-triazaspiro[4.5]decan-3-yl)-1-methyl-cyclohexanecarboxylic acid (40.6 g, 93.4 mmol, 9:1 mixture of trans:cis isomers) in EtOH (400 mL) at 17° C., which induces a 7° C. exotherm. Heat the mixture to 38° C.; then allow the exothermic reaction to heat the mixture to 47° C. Cool the mixture to 35° C. and add additional acetyl chloride (10 mL, 139 mmol) drop-wise to the slurry. Heat the mixture to 40° C. for 1.5 hrs and add additional acetyl chloride (8 mL, 111.4 mmol). Stir the mixture at 40° C. for 12 hrs. Add additional acetyl chloride (8 mL, 111.4 mmol) and EtOH (100 mL). Stir the slurry for an additional 60 min. Cool the mixture to rt and concentrate under reduced pressure to provide a residue. Suspend the residue in MTBE (400 mL); stir for 30 min, and then filter to collect the solid. Dry the solid under vacuum at 45° C. for 2.5 hrs. Suspend the solid in acetone (40 volumes of 95:5 acetone/water) and heat to 50° C. Stir overnight (ca. 12 hrs); then cool the suspension to 27° C. Filter and dry the solid under vacuum at 40° C. to give the title compound as a white solid (24.4 g, 69% yield; 99.5/0.5 mixture of trans:cis isomers). ES/MS m/z 324 (M+H).

PREPARATION 17 tert-Butyl 4-amino-4-[[(4-ethoxycarbonyl-4-ethyl-cyclohexyl)amino]methyl]piperidine-1-carboxylate

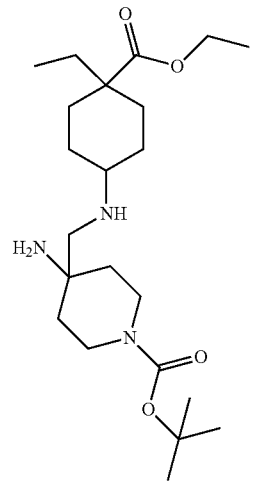 [SMILES: CCOC(=O)C1(CC)CCC(NCC2(N)CCN(C(=O)OC(C)(C)C)CC2)CC1]

Dissolve tert-butyl 4-amino-4-(aminomethyl)piperidine-1-carboxylate (1.4 g, 5.7 mmol), ethyl 1-ethyl-4-oxo-cyclohexanecarboxylate (1.4, 5.7 mmol) and acetic acid (0.3 mL, 5.7 mmol) in DCM (5.7 mL) at rt. After 30 min, add sodium triacetoxyborohydride (1.6 g, 7.5 mmol) and stir the mixture at rt for 18 hrs. Dilute the mixture with DCM (200 mL), and wash with saturated aqueous solution of NaHCO₃ (100 mL). Dry the organic phase over Na₂SO₄; filter, and remove the solvent from the filtrate to give the title compound as a brown oil in quantitative yield (mixture of cis/trans isomers). This material can be used in the next step without any further purification. ES/MS m/z 412 (M+H).

PREPARATION 18 tert-Butyl 3-(4-ethoxycarbonyl-4-ethyl-cyclohexyl)-2-oxo-1,3,8-triazaspiro[4.5]decane-8-carboxylate

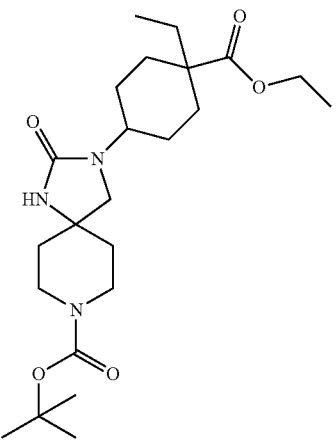 [SMILES: CCOC(=O)C1(CC)CCC(N2CC3(CCN(C(=O)OC(C)(C)C)CC3)NC2=O)CC1]

Add 1,1'-carbonyldiimidazole (6.3 g, 39.0 mmol) to a solution of tert-butyl 4-amino-4-[[(4-ethoxycarbonyl-4-ethyl-cyclohexyl)amino]methyl]piperidine-1-carboxylate (3.2 g, 7.8 mmol, mixture of cis/trans isomers) in DCM (1.6 mL). Stir the mixture at rt for 72 hrs. Dilute the mixture with DCM (500 mL) and wash the mixture with 1N aqueous HCl (2×100 mL). Combine the organic extracts and wash with brine. Dry over Na₂SO₄; filter, and remove the solvent from the filtrate to give the title compound as a brown oil (35% yield as a mixture of cis/trans isomers). This material can be used in the next step without any further purification. ES/MS m/z 438 (M+H).

PREPARATION 19

Ethyl 1-ethyl-4-(2-oxo-1,3,8-triazaspiro[4.5]decan-3-yl)cyclohexanecarboxylate

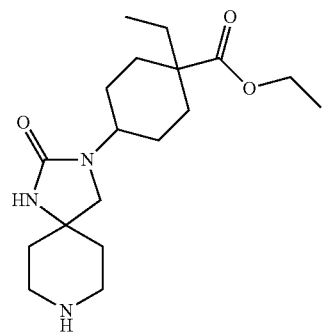 [SMILES: CCOC(=O)C1(CC)CCC(N2CC3(CCNCC3)NC2=O)CC1]

Prepare the title compound essentially by the method of Preparation 11 in 30% yield (mixture of cis/trans isomers) starting from tert-butyl 3-(4-ethoxycarbonyl-4-ethyl-cyclohexyl)-2-oxo-1,3,8-triazaspiro[4.5]decane-8-carboxylate (mixture of cis/trans isomers). ES/MS m/z 338 (M+H).

PREPARATION 20

2-Cyclopropyl-5-ethoxy-4-methyl-benzaldehyde

Add cyclopropylboronic acid (10.6 g, 123 mmol), and potassium phosphate tribasic (67 g, 309.3 mmol) as solids to a solution of 2-bromo-5-ethoxy-4-methyl-benzaldehyde (25 g, 102.84 mmol) in toluene (500 mL) at 24° C. Dilute the mixture with water (10 mL) and sparge the mixture with N₂ for 10-15 min Add 1,1'-[bis(diphenylphosphino)ferrocene]-palladium(II)dichloride dichloromethane complex (0.86 g, 1.0 mmol) and continue the N₂ sparge for an additional 10 min Heat the resulting mixture to 90-100° C. for 2 hrs under a N₂ atmosphere. Cool the mixture to rt; dilute with EtOAc and filter through a plug of diatomaceous earth/silica gel eluting with EtOAc. Wash the resulting filtrate twice with water and then with brine. Dry the organic layer over Na₂SO₄. Filter, collect the filtrate and concentrate the filtrate to provide a dark oil. Subject the dark oil to silica gel chromatography eluting with 20% EtOAc in hexanes to provide the title compound as a pale yellow syrup (20 g, 95% yield). ES/MS m/z 205 (M+H).

PREPARATION 21

5-Ethoxy-2-isopropyl-4-methyl-benzaldehyde

Sparge a solution of 2-bromo-5-ethoxy-4-methyl-benzaldehyde (500 mg, 2.06 mmol) and dichloro[1,3-bis(2,6-di-3-pentylphenyl)imidazol-2-ylidene] (3-chloropyridyl)palladium(II) (34.3 mg, 0.041 mmol) in THF (8 mL) with N₂ for 10 min. Then drop-wise add 0.5 M 2-propylzinc bromide in THF (6 mL, 3.1 mmol). Heat the mixture to 60° C. and stir for 1 hr. Evaporate the solvent under reduced pressure. Dissolve the residue in DCM and filter through a celite plug. Evaporate the solvents from the filtrate under reduced pressure. Subject the residue to flash chromatography (silica gel, 40 g column) eluting with hexanes/EtOAc (gradient of 0 to 15% in EtOAc) to give the title compound as an amber oil (490 mg, 98% yield). ES/MS m/z 207 (M+H).

PREPARATION 22

5-Ethoxy-2-ethyl-4-methyl-benzaldehyde

Under an atmosphere of N₂ combine 2-bromo-5-ethoxy-4-methyl-benzaldehyde (5 g, 102.84 mmol), cesium carbonate (20.11 g, 61.7 mmol), 1,1'-bis(diphenylphosphino) ferrocene-palladium(II)dichloride dichloromethane complex (0.514 g, 0.62 mmol) and THF (41.1 mL). Sparge the mixture with N₂ for 10 min and maintain the reaction under an N₂ atmosphere. Add a 1M solution of triethylborane in THF (61.7 mL, 61.7 mmol). Stir the resulting mixture at 70° C. overnight. Then add acetic acid (50% in water, 3 mL) and stir the mixture at 70° C. for 20 min Cool the mixture to rt and filter through a plug of celite rinsing the celite with EtOAc. Wash the organic layer twice with water and then with brine. Dry over Na₂SO₄; filter, and remove the solvent from the filtrate under reduced pressure. Subject the residue to flash chromatography (silica gel, 220 g column) eluting with hexane/EtOAc (gradient from 0 to 15% in EtOAc). Combine the desired fractions and remove the solvent under reduced pressure to give the title compound as a pale yellow oil (3.1 g, 74% yield). $^1$H NMR (300 MHz, CDCl₃) δ 10.26

(s, 1H), 7.26 (s, 1H), 7.04 (s, 1H), 4.08 (q, 2H), 2.95 (q, 2H), 2.26 (s, 3H), 1.43 (t, 3H), 1.25 (t, 3H).

PREPARATION 23

5-Ethoxy-4-methyl-2-propyl-benzaldehyde

Add dicyclohexyl-[3-(2,6-dimethoxyphenyl)phenyl]phosphane (3.8 g, 9.3 mmol) and tris(dibenzylideneacetone)dipalladium(0) (3.8 g, 4.1 mmol) to a biphasic (solid/liquid) mixture of tribasic potassium phosphate (265 g, 1250 mmol), propylboronic acid (100 g, 1140 mmol), and 2-bromo-5-ethoxy-4-methyl-benzaldehyde (101 g, 415 mmol) in degassed toluene (2 L) at 22° C. Heat the mixture to 90° C., and stir for 30 min Cool the resulting green mixture to 40° C. Filter through diatomaceous earth eluting with 1.5 L of toluene. Concentrate the filtrate under reduced pressure. Dilute the resulting residue with DCM (600 mL), then add SiliaMet®Thiol (135 g). Stir the mixture overnight. Filter the mixture through diatomaceous earth eluting with methylene chloride. Concentrate the filtrate and filter through a 1.0 kg pad of silica gel eluting with hexanes/DCM (50/50 to 100 DCM). Collect 1.0 L fractions. Combine the desired fractions and concentrate under reduced pressure to give the title compound as a yellow oil (77.4 g, 90% yield). ES/MS m/z 207 (M+H).

PREPARATION 24

5-Cyclopropyl-2-ethyl-4-methoxy-benzaldehyde

Add cyclopropylboronic acid (1.22 g, 14.19 mmol) and potassium fluoride (1.09 g, 18.92 mmol) as solids to a solution of 5-bromo-2-ethyl-4-methoxy-benzaldehyde (2.5 g, 9.46 mmol) in 1,4-dioxane (31.5 mL) at 24° C. Degass and sparge the mixture with $N_2$ for 10-15 min. Add 1,1'-bis(diphenylphosphino)ferrocene-palladium(II)dichloride dichloromethane complex (0.237 g, 0.284 mmol) and continue the $N_2$ sparge for 10 minutes. Heat the resulting mixture to 100° C. overnight under an $N_2$ atmosphere. Cool the mixture to rt and dilute with EtOAc. Filter through a celite plug and rinse the celite with EtOAc. Wash the filtrate with water and brine. Dry over $Na_2SO_4$, filter and evaporate the solvent from the filtrate to give a dark oil. Subject the dark oil to flash chromatography (silica gel, 80 g column) eluting with hexanes/EtOAc (gradient from 0 to 15% in EtOAc) to give the title compound as a colorless oil (1.8 g, 88% yield). ES/MS m/z 205 (M+H).

PREPARATION 25

2-Fluoro-5-isopropyl-4-methyl-benzaldehyde

Degassed and sparge a solution of 5-bromo-2-fluoro-4-methyl-benzaldehyde (7.0 g, 32.2 mmol) in THF (129 mL) with $N_2$ for 10-15 minutes. Drop-wise add dichloro[1,3-bis(2,6-di-3-pentylphenyl)imidazol-2-ylidene] (3-chloropyridyl)palladium(II) (0.54 g, 0.64 mmol) and 0.5M 2-propylzinc bromide in THF (100 mL). Stir the mixture at 50° C. for 90 min. Cool the mixture to rt. Add water (60 mL). Extract the mixture with EtOAc. Wash the organic extracts with water and brine. Dry over $Na_2SO_4$; filter and evaporate the solvent from the filtrate under reduced pressure to give a residue. Subject the residue to flash chromatography (silica gel, 50 g column) eluting with hexanes/MTBE (9:1) to give the title compound as a yellow oil (4.82 g, 83% yield). $^1$H NMR (300 MHz, $CDCl_3$) δ 10.29 (s, 1H), 7.72 (d, 1H, J=7.2 Hz), 6.93 (d, 1H, J=11.1 Hz), 3.08 (sept, 1H), 2.39 (s, 3H), 1.22 (d, 6H).

PREPARATION 26

Methyl 4-chloro-5-isopropenyl-2-methoxy-benzoate

Add potassium isopropenyltrifluoroborate (2.45 g, 16.1 mmol), potassium carbonate (4.5 g, 32.2 mmol), water (5 mL) and tetrakis(triphenylphosphine)palladium(0) (1.24 g, 1.07 mmol) to a solution of methyl 5-bromo-4-chloro-2-methoxy-benzoate (3 g, 10.73 mmol) in 1,4-dioxane (54 mL) under an $N_2$ atmosphere. Sparge the mixture with $N_2$ for 15 minutes. Maintain the mixture under a $N_2$ atmosphere and heat to 70° C. for 16 hours. Dilute the mixture with EtOAc; filter through a celite plug, and wash the celite with EtOAc. Collect the organic filtrate; sequentially wash with water, 1N aqueous hydrochloric acid, and aqueous saturated solution of $NaHCO_3$. Dry over $MgSO_4$, filter and evaporate the solvent from the filtrate under reduced pressure. Subject the residue to flash chromatography (silica gel, 40 g column) eluting with hexane/EtOAc (gradient from 0% to 20% of EtOAc). Collect the desired fractions and remove the solvent under reduced pressure to give the title compound as a yellow viscous oil (2.45 g, 78% yield). ES/MS m/z 241 (M+H).

PREPARATION 27

Methyl 4-chloro-5-isopropyl-2-methoxy-benzoate

Combine methyl 4-chloro-2-methoxy-5-isopropenyl-benzoate (2.47 g, 8.42 mmol), EtOH (34 mL) and 10% platinum on carbon (0.30 g, 0.156 mmol). Stir the mixture under a $H_2$ atmosphere at rt for 48 hrs. Filter the mixture through a celite plug. Evaporate the solvent from the filtrate under vacuum to provide a solid. Subject the solid to flash chromatography (Varian, silica gel, 40 g column) eluting with hexane/EtOAc (gradient from 0% to 20% of EtOAc). Collect the desired fractions and remove the solvent under reduced pressure to give the title compound as a colorless oil (2.38 g, 72% yield).

PREPARATION 28

(4-Chloro-5-isopropyl-2-methoxy-phenyl) methanol

Slowly add 1M lithium aluminium hydride in THF (8.04 mL, 8.04 mmol) to an ice-cooled solution of methyl 4-chloro-5-isopropyl-2-methoxy-benzoate (2.38 g, 8.04 mmol) in THF (10 mL). Allow the mixture to warm to rt and stir for 16 hours. Add water (0.6 mL), 1N aqueous sodium hydroxide (0.6 mL) and water (1.2 mL) at 0° C. to quench the reaction. Stir the mixture for 3 hours at 0° C. Dilute the suspension with dichloromethane. Filter through a celite plug and wash the celite with DCM. Remove the solvent from the filtrate under reduced pressure. Dilute the residue with DCM (30 mL) and wash with water (30 mL). Separate the layers and wash the organic phase with brine (30 mL). Combine the organic layers. Dry over $MgSO_4$, filter and remove the solvent from the filtrate under reduced pressure to provide the title compound as a colorless oil (1.98 g, 97% yield). ES/MS m/z 215 (M+H).

PREPARATION 29

4-Chloro-5-isopropyl-2-methoxy-benzaldehyde

Add $MnO_2$ (8.02 g, 78.4 mmol) to a stirring solution of (4-chloro-5-isopropyl-2-methoxy-phenyl)methanol (1.98 g, 7.84 mmol) in DCM (50 mL). After 5 hours, add a second portion of $MnO_2$ (4.01 g, 39.2 mmol) at rt. Stir the mixture at rt for 16 hours. Dilute the mixture with DCM and filter through a celite plug washing the celite with DCM. Collect the filtrate and remove the solvent under reduced pressure to give the title compound as a white solid (1.4 g, 73% yield). ES/MS m/z 213 (M+H).

PREPARATION 30

Methyl 4-[8-[(2-cyclopropyl-5-ethoxy-4-methyl-phenyl)methyl]-2-oxo-1,3,8-triazaspiro[4.5]decan-3-yl]benzoate

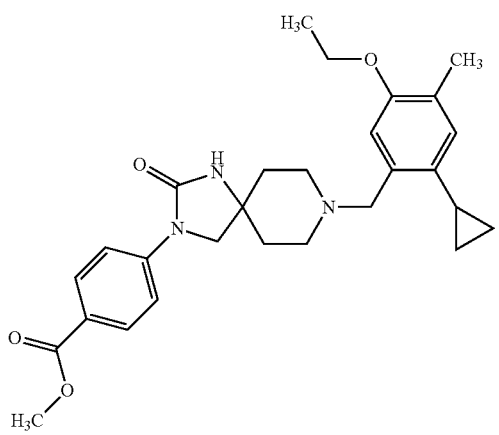 [SMILES: CCOc1cc(CN2CCC3(CC2)CN(c2ccc(C(=O)OC)cc2)C(=O)N3)c(C2CC2)cc1C]

Suspend methyl 4-(2-oxo-1,3,8-triazaspiro[4.5]decan-3-yl)benzoate hydrochloride (375 g, 1151 mmol) in DCM (8.5 L) at 20° C., add trimethylamine (485 mL, 3480 mmol) and a DCM solution of 2-cyclopropyl-5-ethoxy-4-methyl-benzaldehyde (235.5 g, 1153 mmol; 500 mL of DCM). Cool the suspension to 20° C. and add sodium triacetoxyborohydride (732 g, 3454 mmol) in ca. 100 g portions over a 3.5 hr period while maintaining the internal temperature below 24° C. Stir the resulting suspension for 12 hr (100% conversion). Cool the suspension to 15° C. Add water (8.5 L) drop-wise, while maintaining an internal temperature below 25° C. to form a biphasic solution. Separate the resulting layers and wash the organic layer (ca. 10 L) with water (10 L). Separate the resulting layers and concentrate the organic layer to about 2 L to provide a thick suspension. Dilute the suspension with MeOH (4 L) and distill to reduce the solvent amount to about 3 L. Cool the suspension to 5° C.; stir for 30 min and filter to collect the solid. Rinse the solid with MeOH (1.5 L). Dry the solid under a stream of $N_2$ at 23° C., pulling slight vacuum with a $N_2$ bleed (nitrogen press) to provide the title compound as a white solid (452 g, 82% yield). ES/MS m/z 478.2 (M+H).

PREPARATIONs 31-36

The compounds of Preparations 31-36 are prepared essentially as described in Preparation 30 from the corresponding piperidine and aldehyde derivatives.

TABLE 1

| Prep. No. | Structure | Chemical name | Yield (%) | ES/MS m/z |
|---|---|---|---|---|
| 31 | 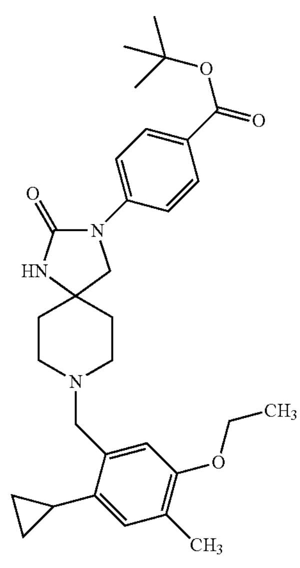 [SMILES: CCOc1cc(CN2CCC3(CC2)CN(c2ccc(C(=O)OC(C)(C)C)cc2)C(=O)N3)c(C2CC2)cc1C] | tert-Butyl 4-[8-[(2-cyclopropyl-5-ethoxy-4-methyl-phenyl)methyl]-2-oxo-1,3,8-triazaspiro[4.5]decan-3-yl]benzoate | 75 | 520 (M + H) |

TABLE 1-continued

| Prep. No. | Structure | Chemical name | Yield (%) | ES/MS m/z |
|---|---|---|---|---|
| 32 | 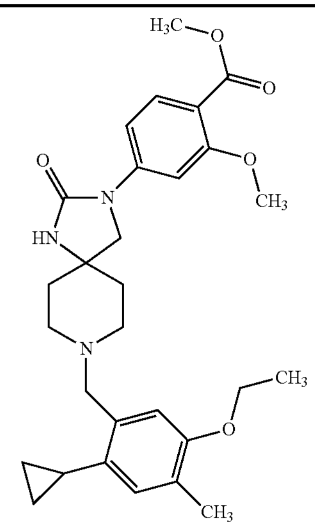 | Methyl 4-[8-[(2-cyclopropyl-5-ethoxy-4-methyl-phenyl)methyl]-2-oxo-1,3,8-triazaspiro[4.5]decan-3-yl]-2-methoxy-benzoate | 84 | 508.2 (M + H) |
| 33 | 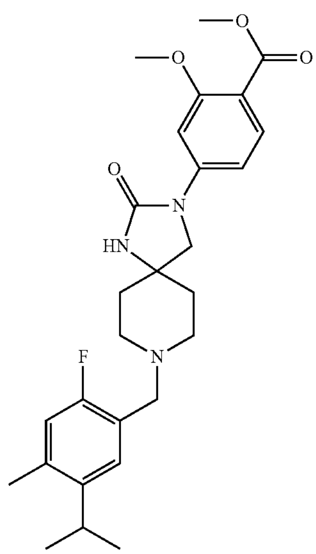 [SMILES: COC(=O)c1ccc(N2CC3(CCN(Cc4cc(C(C)C)c(C)cc4F)CC3)NC2=O)cc1OC] | Methyl 4-[8-[(2-fluoro-5-isopropyl-4-methyl-phenyl)methyl]-2-oxo-1,3,8-triazaspiro[4.5]decan-3-yl]-2-methoxy-benzoate | 75 | 484 (M + H) |
| 34 | 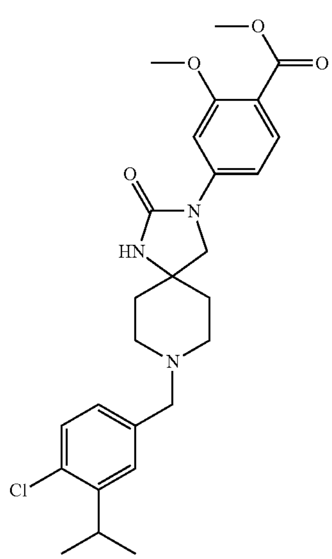 [SMILES: COC(=O)c1ccc(N2CC3(CCN(Cc4ccc(Cl)c(C(C)C)c4)CC3)NC2=O)cc1OC] | Methyl 4-[8-[(4-chloro-3-isopropyl-phenyl)methyl]-2-oxo-1,3,8-triazaspiro[4.5]decan-3-yl]-2-methoxy-benzoate | 72 | 486 (M + H) |

TABLE 1-continued

| Prep. No. | Structure | Chemical name | Yield (%) | ES/MS m/z |
|---|---|---|---|---|
| 35 | 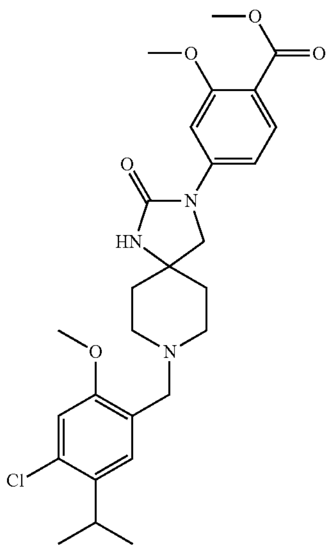 [SMILES: COC(=O)c1ccc(N2CC3(CCN(Cc4cc(C(C)C)c(Cl)cc4OC)CC3)NC2=O)cc1OC] | Methyl 4-[8-[(4-chloro-5-isopropyl-2-methoxy-phenyl)methyl]-2-oxo-1,3,8-triazaspiro[4.5]decan-3-yl]-2-methoxy-benzoate | 70 | 516 (M + H) |
| 36 | 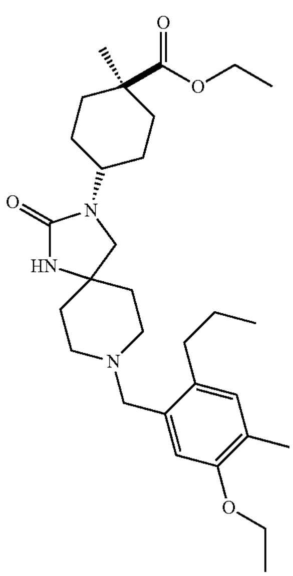 | Ethyl trans-4-[8-[(5-ethoxy-4-methyl-2-propyl-phenyl)methyl]-2-oxo-1,3,8-triazaspiro[4.5]decan-3-yl]-1-methyl-cyclohexanecarboxylate | 76 | 514.4 (M + H) |

PREPARATION 37

Ethyl trans-4-[8-[(2-cyclopropyl-5-ethoxy-4-methyl-phenyl)methyl]-2-oxo-1,3,8-triazaspiro[4.5]decan-3-yl]-1-methyl-cyclohexanecarboxylate and Ethyl cis-4-[8-[(2-cyclopropyl-5-ethoxy-4-methyl-phenyl)methyl]-2-oxo-1,3,8-triazaspiro[4.5]decan-3-yl]-1-methyl-cyclohexanecarboxylate

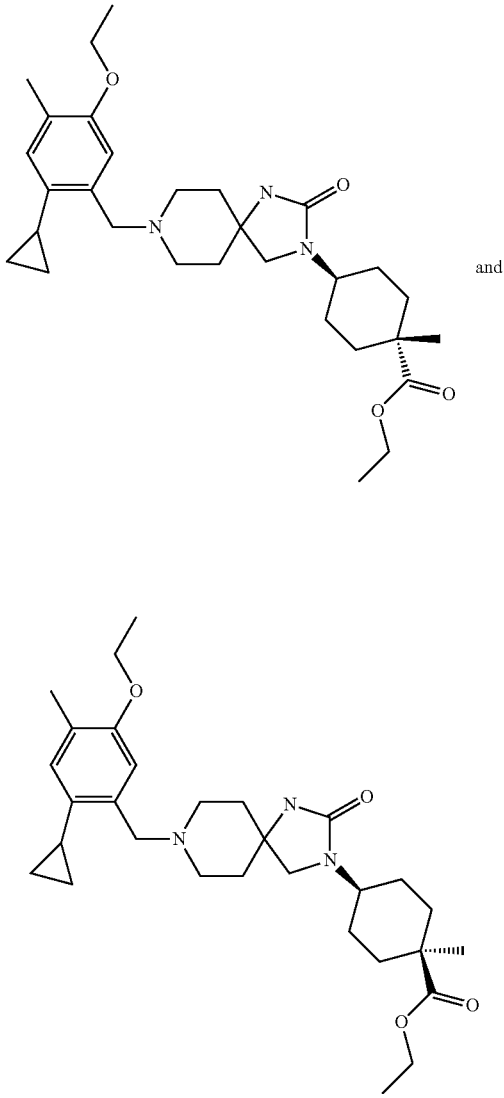

and

The title compounds are prepared essentially as described in Preparation 30 by using ethyl 1-methyl-4-(2-oxo-1,3,8-triazaspiro[4.5]decan-3-yl)cyclohexanecarboxylate hydrochloride (26.6 g, 73.91 mmol, as a 60/40 mixture of cis/trans isomers) and 2-cyclopropyl-5-ethoxy-4-methyl-benzaldehyde as starting materials to give the title compounds (42.8 g, 60/40 mixture of cis/trans isomers). ES/MS m/z 512 (M+H).

The cis and trans isomers can be separated by dissolving the mixture of isomers in MeOH (400 mL) and DCM (20 mL) and subjecting the mixture to chiral chromatography [Instrument: Novasep Supersep 400; Column. Chiralpak AD (50×250 mm, 5 μm); using a mobile phase: $CO_2$(A)/MeOH with 0.2% DMEA (B); Elution Mode: Isocratic 25% B; flow rate: 302 g/min (103 mL/min of B); outlet pressure: 100 bar; column oven temperature: 35° C. Guide collection: by time; Detection: UV @ 220 nm; Loading: 370 mg/injection (injections every 5 min) to give the trans isomer (15.8 g, 32% yield, 2nd eluting isomer) and the cis isomer (24.7 g, 50% yield 1st eluting isomer).

Analytical chiral column conditions: [Instrument: Waters SFC/UV(PDA)/MS; Column: Chiralpak AD (4.6×100 mm, 5 μm); Mobile phase: $CO_2$(A)/MeOH with 0.2% isopropylamine (B); Elution Mode: Isocratic 25% B; Flow rate: 5 mL/min; outlet pressure: 150 bar; column oven temperature: 40° C.; Detection: UV-PDA (monitoring @ 220 and 254 nm) and MS (APCI positive and negative modes); Run Time: 2 min; Retention Times (min): 0.79 (1st eluting isomer=cis isomer) and 1.38 min (2nd eluting isomer=trans isomer).

PREPARATION 38

Methyl 4-[8-[(5-ethoxy-2-ethyl-4-methyl-phenyl)methyl]-2-oxo-1,3,8-triazaspiro[4.5]decan-3-yl]-2-methoxy-benzoate

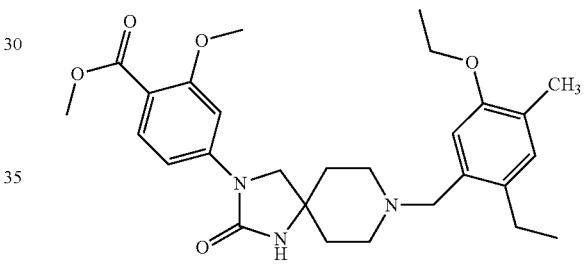

Add triethylamine (3.37 mL, 24.2 mmol) to a suspension of methyl-2-methoxy-4-(2-oxo-1,3,8-triazaspiro[4.5]-decan-3-yl)benzoate hydrochloride (4.3 g, 12.1 mmol) in dichloroethane (60.4 mL) under nitrogen at rt and stir for 10 minutes. Add 2-ethyl-5-ethoxy-4-methyl-benzaldehyde (2.63 g, 13.3 mmol) and stir for 15 minutes. Then add sodium triacetoxyborohydride (4.04 g, 18.1 mmol) and stir the mixture at 70° C. overnight. Dilute the mixture with DCM (250 mL). Sequentially wash the mixture with aqueous saturated solution of $NaHCO_3$ (50 mL), water (100 mL), and brine. Separate the layers and dry the organic phase over $Na_2SO_4$; filter, and concentrate the filtrate under reduced pressure. Subject the residue to flash chromatography (silica gel, 120 g) eluting with hexane/EtOAc (gradient from 0 to 100% in EtOAc) and then, DCM/MeOH (from 0 to 10% in MeOH) to give the title compound as a gummy colorless oil (100% yield). ES/MS m/z 496 (M+H).

PREPARATION 39-42

The compounds of Preparations 39-42 are prepared essentially as described in Preparation 38 from the corresponding piperidine and aldehyde derivatives.

TABLE 2

| Prep. No. | Structure | Chemical name | Yield (%) | ES/MS m/z |
|---|---|---|---|---|
| 39 | 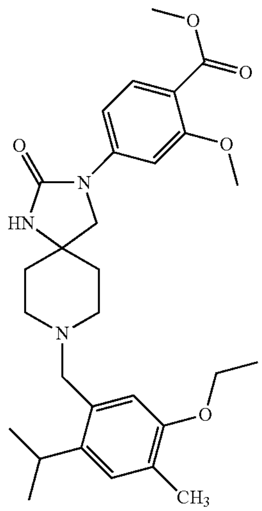 [SMILES: CCOc1cc(CN2CCC3(CC2)CN(c2ccc(C(=O)OC)c(OC)c2)C(=O)N3)c(C(C)C)cc1C] | Methyl 4-[8-[(5-ethoxy-2-isopropyl-4-methyl-phenyl)methyl]-2-oxo-1,3,8-triazaspiro[4.5]decan-3-yl]-2-methoxy-benzoate | 25 | 510 (M + H) |
| 40 | 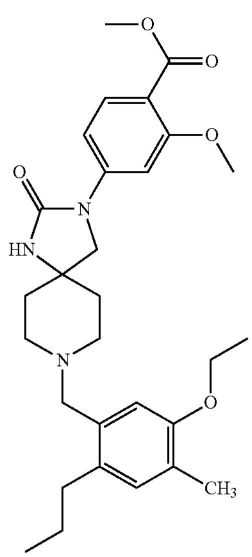 [SMILES: CCCc1cc(C)c(OCC)cc1CN1CCC2(CC1)CN(c1ccc(C(=O)OC)c(OC)c1)C(=O)N2] | Methyl 4-[8-[(5-ethoxy-4-methyl-2-propyl-phenyl)methyl]-2-oxo-1,3,8-triazaspiro[4.5]decan-3-yl]-2-methoxy-benzoate | 98 | 510 (M + H) |

TABLE 2-continued

| Prep. No. | Structure | Chemical name | Yield (%) | ES/MS m/z |
|---|---|---|---|---|
| 41 | 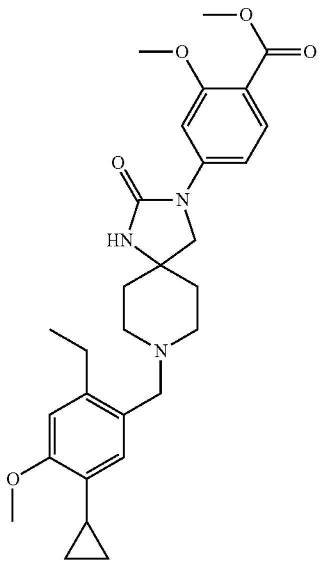 [SMILES: CCc1cc(OC)c(C2CC2)cc1CN1CCC2(CC1)CN(c1ccc(C(=O)OC)c(OC)c1)C(=O)N2] | Methyl 4-[8-[(5-cyclopropyl-2-ethyl-4-methoxy-phenyl)methyl]-2-oxo-1,3,8-triazaspiro[4.5]decan-3-yl]-2-methoxy-benzoate | 68 | 508 (M + H) |
| 42 | 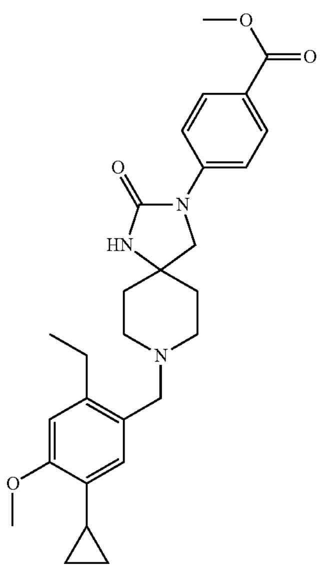 [SMILES: CCc1cc(OC)c(C2CC2)cc1CN1CCC2(CC1)CN(c1ccc(C(=O)OC)cc1)C(=O)N2] | Methyl 4-[8-[(5-cyclopropyl-2-ethyl-4-methoxy-phenyl)methyl]-2-oxo-1,3,8-triazaspiro[4.5]decan-3-yl]benzoate | 32 | 478 (M + H) |

PREPARATION 43 tert-Butyl 4-[8-[(5-ethoxy-2-isopropyl-4-methyl-phenyl)methyl]-2-oxo-1,3,8-triazaspiro[4.5]decan-3-yl]benzoate

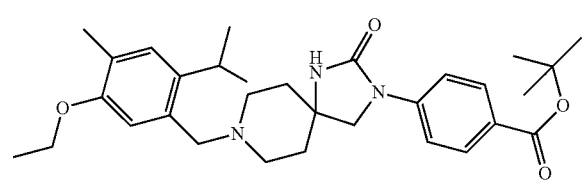 [SMILES: CCOc1cc(CN2CCC3(CC2)CN(c2ccc(C(=O)OC(C)(C)C)cc2)C(=O)N3)c(C(C)C)cc1C]

Add triethylamine (0.3 mL, 2.2 mmol) to a suspension of tert-butyl 4-(2-oxo-1,3,8-triazaspiro[4.5]-decan-3-yl)benzoate hydrochloride (0.40 g, 1.09 mmol) in DCM (5.4 mL) under N₂ at rt. Stir the mixture for 10 minutes. Then, add 5-ethoxy-2-isopropyl-4-methyl-benzaldehyde (0.25 g, 1.2 mmol) and stir for 15 min Finally, add sodium triacetoxyborohydride (0.36 g, 1.63 mmol) and stir the mixture at rt overnight. If additional starting material is left, add sodium triacetoxyborohydride (0.2 g) and stir the mixture at 70° C. overnight. Dilute the mixture with DCM (100 mL). Sequentially wash the mixture with aqueous saturated solution of NaHCO₃ (50 mL), water (30 mL), and brine. Dry the organic phase over Na₂SO₄; filter and concentrate the filtrate under reduced pressure. Subject residue to flash chromatography (silica gel, 40 g) eluting with hexane/EtOAc (gradient from 0 to 100% in EtOAc) and then DCM/MeOH (from 0 to 10% in MeOH) to afford the title compound as a pale cream solid (450 mg, 75% yield). ES/MS m/z 522 (M+H).

PREPARATION 44

Ethyl trans-4-[8-[(5-cyclopropyl-2-ethyl-4-methoxyphenyl)methyl]-2-oxo-1,3,8-triazaspiro[4.5]decan-3-yl]-1-methyl-cyclohexanecarboxylate and Ethyl cis-4-[8-[(5-cyclopropyl-2-ethyl-4-methoxyphenyl)methyl]-2-oxo-1,3,8-triazaspiro[4.5]decan-3-yl]-1-methyl-cyclohexanecarboxylate

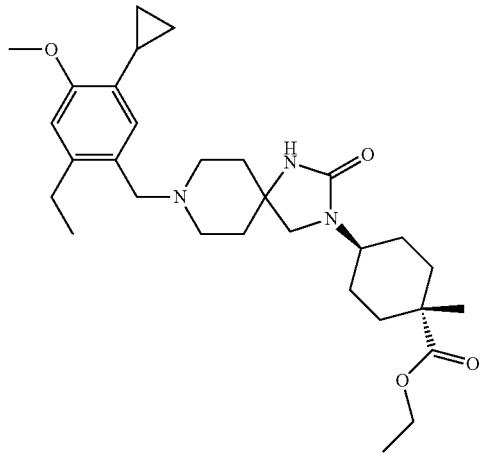

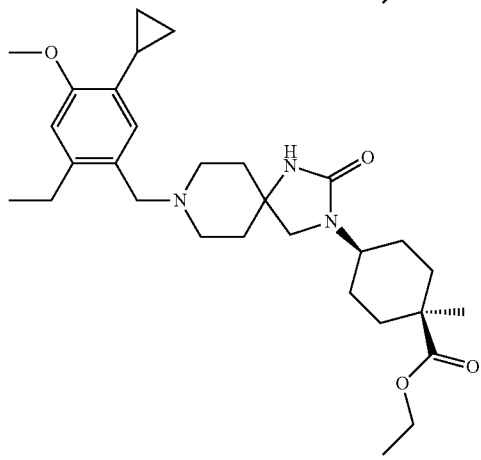

Add sodium triacetoxyborohydride (0.5 g, 2.6 mmol) to a mixture of ethyl 1-methyl-4-(2-oxo-1,3,8-triazaspiro[4.5]decan-3-yl)cyclohexanecarboxylate (0.5 g, 1.5 mmol as a mixture of cis/trans isomers) and 5-cyclopropyl-2-ethyl-4-methoxy-benzaldehyde (0.3 g, 1.5 mmol) in DCM (3.0 mL) for 10 min at rt. Add sodium triacetoxyborohydride (0.5 g, 2.6 mmol). Stir the mixture for 16 h at rt. Evaporate the solvent under vacuum and dissolve the residue in EtOAc. Sequentially wash with water and brine. Dry the organic phase over $Na_2SO_4$; filter and evaporate the solvent from the filtrate to give a residue containing a mixture of cis/trans isomers in an aprox ratio 66/34. Subject the residue to flash chromatography (silica gel) eluting with ethanol/DCM (gradient from 0% to 13% in ethanol). Collect the appropriate fractions and evaporate to dryness to obtain the crude material as a mixture of cis and trans-isomers. Separate the cis and trans isomers by chiral chromatography on a Chiralpak AD column (5 um, 2×25 cm) eluting with ($CO_2$(A)/MeOH-DMEA (0.2%)(B) Isocratic 25%) to give the trans isomer as a white solid (113 mg, 14% yield) and the cis isomer as a white solid (240 mg, 30 yield). ES/MS m/z 512 (M+H).

PREPARATION 45

Ethyl trans-4-[8-[(2-cyclopropyl-5-ethoxy-4-methylphenyl)methyl]-2-oxo-1,3,8-triazaspiro[4.5]decan-3-yl]-1-ethyl-cyclohexanecarboxylate and Ethyl cis-4-[8-[(2-cyclopropyl-5-ethoxy-4-methylphenyl)methyl]-2-oxo-1,3,8-triazaspiro[4.5]decan-3-yl]-1-ethyl-cyclohexanecarboxylate

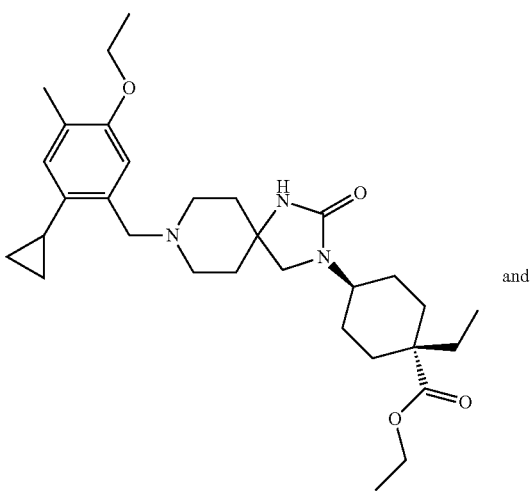

and

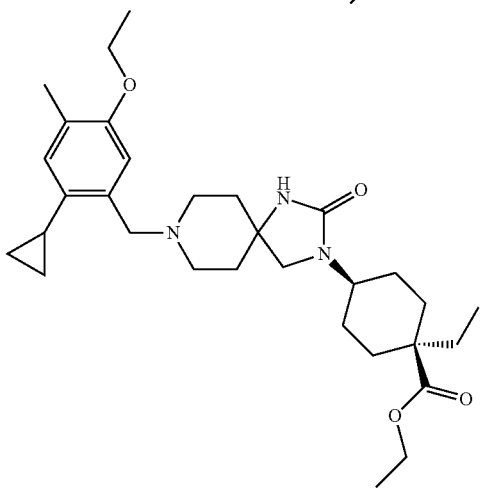

Prepare the title compounds essentially as described in Preparation 44 using ethyl 1-ethyl-4-(2-oxo-1,3,8-triazaspiro[4.5]decan-3-yl)cyclohexanecarboxylate (0.91 g, 2.7 mmol, as a mixture of cis/trans isomers) and 2-cyclopropyl-5-ethoxy-4-methyl-benzaldehyde (0.56 g, 2.7 mmol) as starting materials to give a crude material containing a mixture of cis/trans isomers in an aprox. ratio of 67/33. Separate the isomers essentially as described in Preparation 44 to provide the trans isomer of the title compound as a white solid (100 mg, 7% yield) and the cis isomer of the title compound as a white solid (240 mg, 17% yield). ES/MS m/z 526 (M+H).

EXAMPLE 1

4-[8-[(2-Cyclopropyl-5-ethoxy-4-methyl-phenyl)methyl]-2-oxo-1,3,8-triazaspiro[4.5]decan-3-yl]benzoic acid hydrochloride

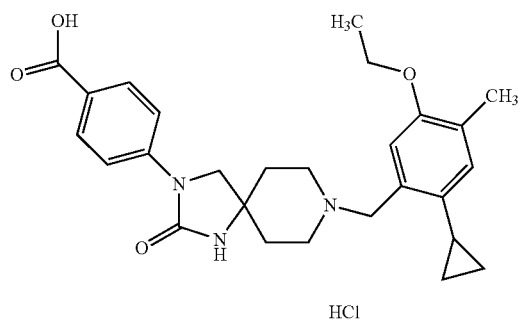 [SMILES: CCOc1cc(CN2CCC3(CC2)CN(c2ccc(C(=O)O)cc2)C(=O)N3)c(C2CC2)cc1C ; Cl]

Add 4M HCl in 1,4-dioxane (300 mL, 1200 mmol) to a suspension of tert-butyl 4-[8-[(2-cyclopropyl-5-ethoxy-4-methyl-phenyl)methyl]-2-oxo-1,3,8-triazaspiro[4.5]decan-3-yl]benzoate (35 g, 57.24 mmol) in DCM (300 mL). Stir the resulting mixture for 12 h under a nitrogen atmosphere. Filter the resulting thick slurry. Collect the solid and dry it to constant weight in a vacuum oven at 60° C. Suspend the solid in acetone (300 mL) and stir overnight at rt, dilute with acetone (300 mL), stir an additional 30 min, and filter, rinsing with acetone (4×100 mL). Dry the resulting white solid in a vacuum oven overnight at 60° C., to afford the title compound as a white solid (26.3 g, 89% yield). ES/MS m/z 464 (M+H).

EXAMPLE 2

4-[8-[(2-Cyclopropyl-5-ethoxy-4-methyl-phenyl)methyl]-2-oxo-1,3,8-triazaspiro[4.5]decan-3-yl]benzoic acid hydrate

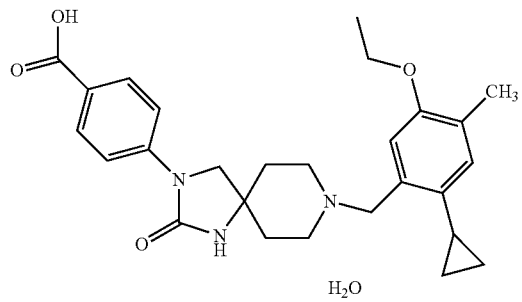

Suspend methyl 4-[8-[(2-cyclopropyl-5-ethoxy-4-methyl-phenyl)methyl]-2-oxo-1,3,8-triazaspiro[4.5]decan-3-yl]benzoate (430 g, 900.3 mmol) in MeOH (9 L). Add 5M aqueous NaOH (1.0 L, 5 mol) to the suspension, inducing an internal temperature rise to 28° C. Heat the suspension to 55° C. and stir the suspension for 12 h (97% conversion). Add additional 1M aqueous NaOH (2 L, 2 mol) and increase the internal temperature to 65° C. Stir the mixture for additional 5 hr to provide ca a 99% conversion. Cool the slurry to 15° C. (internal), acidify to pH 7.01 with 5M aqueous HCl (1.4 L), and stir the slurry at rt (ca. 23° C.) for 2 days. Distill off ca. 80% of MeOH via house vacuum (ca. 10 torr; 35° C. jacket temp), and dilute with deionized water (6 L). Adjust the pH to 6.81 with 5M aqueous HCl and stir for 1 h at 23° C. Filter the slurry to collect the white solid and rinse the solid with deionized water (4 L) (filtrate pH=7.12 @ 17.2° C.). Dry the solid under vacuum with a slight $N_2$ bleed (nitrogen press) to constant weight (12 hrs) to provide the title compound as a white solid (435 g, quantitative yield). ES/MS m/z 464 (M+H).

EXAMPLE 3

4-[8-[(2-Cyclopropyl-5-ethoxy-4-methyl-phenyl)methyl]-2-oxo-1,3,8-triazaspiro[4.5]decan-3-yl]benzoic acid tert-butylamine salt

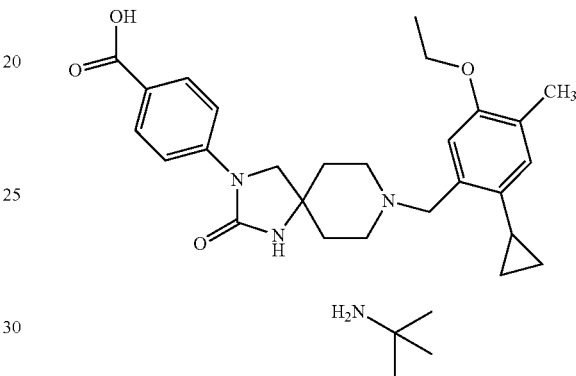

Suspend 4-[8-[(2-cyclopropyl-5-ethoxy-4-methyl-phenyl)methyl]-2-oxo-1,3,8-triazaspiro[4.5]decan-3-yl]benzoic acid hydrate (495 mg, 1.07 mmol) in a mixture of water (14 mL) and THF (6 mL) and stir the slurry at 55° C./500 rpm (probe thermometer temperature). Add tert-butylamine (140 μL, 1.33 mmol). The slurry clarifies to a clear, colorless solution. Add water (15 mL) at a rate of 0.5 mL/min; then cool the sample at 5° C./hour to 20° C. to produce a thick, white slurry. Isolate the white solid using vacuum filtration. Dry the white solid for 30 minutes under an air stream to provide the title compound (454 mg, 79% yield). ESI (positive ion mode)/MS m/z 464.2526 ($M_{acid}$+H), 74.0959 ($M_{counterion}$+H).

EXAMPLE 4

Sodium 4-[8-[(2-cyclopropyl-5-ethoxy-4-methyl-phenyl)methyl]-2-oxo-1,3,8-triazaspiro[4.5]decan-3-yl]benzoate

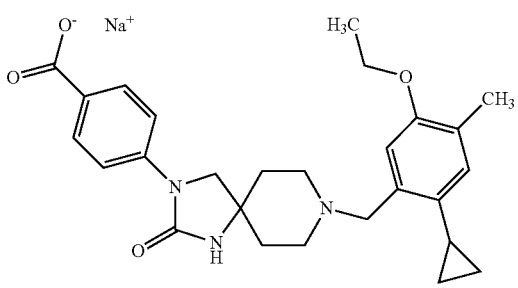 [SMILES: CCOc1cc(CN2CCC3(CC2)CN(c2ccc(C(=O)[O-])cc2)C(=O)N3)c(C2CC2)cc1C ; [Na+]]

Suspend 4-[8-[(2-cyclopropyl-5-ethoxy-4-methyl-phenyl)methyl]-2-oxo-1,3,8-triazaspiro[4.5]decan-3-yl]benzoic acid hydrate (340 g, 733 mmol) in water (6.8 L) and add 5M aqueous NaOH (220 mL, 1100 mmol), maintaining an internal temperature below 28° C. Heat the solution to 65° C. to form a hazy suspension. Add sodium 4-[8-[(2-cyclopropyl-5-ethoxy-4-methyl-phenyl)methyl]-2-oxo-1,3,8-triazaspiro[4.5]decan-3-yl]benzoate salt (56.4 g) as seed to induce crystallization. Slowly cool the slurry to 25° C. and stir for 12 hrs. Filter the slurry to collect the solid; rinse the solid with water (4 L); and dry it under vacuum at 25° C., then at 45° C. in a vacuum oven (10 torr, 3 days) to a constant weight to provide the title compound (371 g, 88% yield). ES/MS m/z 464.2 (M+H).

ALTERNATIVE SYNTHESIS OF EXAMPLE 4

Sodium 4-[8-[(2-cyclopropyl-5-ethoxy-4-methyl-phenyl)methyl]-2-oxo-1,3,8-triazaspiro[4.5]decan-3-yl]benzoate (crystalline form 1)

Suspend 4-[8-[(2-cyclopropyl-5-ethoxy-4-methyl-phenyl)methyl]-2-oxo-1,3,8-triazaspiro[4.5]decan-3-yl]benzoic acid hydrate (25.0 g, 52 mmol) in water (500 mL). Stir the slurry at 65° C./1000 rpm. Add 5M aqueous sodium hydroxide (15 mL, 75 mmol). The sample initially clarifies to a light yellow solution; then over the next few minutes the sample becomes cloudy and eventually develops into a thick slurry of a bright white solid. Cool the slurry to 5° C. The pH is 13. Isolate the white solid by vacuum filtration slowly over two days while maintaining the temperature at 5° C. Rinse the solid with the filtrate and then with water (20 mL). Dry the white solid in a vacuum oven at 70° C. overnight to provide the title compound (23.5 g, 90% yield). The material was crystalline as determined by XRD.

X-Ray Powder: Diffraction Sodium 4-[8-[(2-cyclopropyl-5-ethoxy-4-methyl-phenyl)methyl]-2-oxo-1,3,8-triazaspiro[4.5]decan-3-yl]benzoate salt, form 1

The X-ray powder diffraction (XRD) pattern of crystalline sodium 4-[8-[(2-cyclopropyl-5-ethoxy-4-methyl-phenyl)methyl]-2-oxo-1,3,8-triazaspiro[4.5]decan-3-yl]benzoate, form 1, is obtained on a Bruker D4 Endeavor X-ray powder diffractometer, equipped with a CuKα source (λ=1.54060 Å) and a Vantec detector, operating at 35 kV and 50 mA. Scan the sample between 4 and 40° in 2θ, with a step size of 0.009° in 2θ and a scan rate of 0.5 seconds/step, and with 0.6 mm divergence, 5.28 fixed anti-scatter, and 9.5 mm detector slits. Pack the sample as a dry powder on a quartz sample holder and a smooth surface is obtained using a glass slide. Collect the crystal form diffraction patterns at ambient temperature and relative humidity. A peak position variability of ±0.2 in 2θ may occur due to a variation in the temperature and/or humidity at which the sample is analyzed. Collect the diffraction patterns at ambient temperature and relative humidity, and adjust based on NIST 675 standard peaks at 8.853 and 26.774 degrees 2θ. Confirmation of a crystal form may be made based on any unique combination of distinguishing peaks (in units of ° 2θ), typically the more prominent peaks.

An XRD pattern of sodium 4-[8-[(2-cyclopropyl-5-ethoxy-4-methyl-phenyl)methyl]-2-oxo-1,3,8-triazaspiro[4.5]decan-3-yl]benzoate using CuKα radiation provides the diffraction peaks (2-theta values) as listed in Table 3 below.

TABLE 3

X-ray powder diffraction peaks of crystalline sodium 4-[8-[(2-cyclopropyl-5-ethoxy-4-methyl-phenyl)methyl]-2-oxo-1,3,8-triazaspiro[4.5]decan-3-yl]benzoate

| Peak | Angle (°2θ) +/− 0.2° | Relative Intensity (% of most intense peak) |
|---|---|---|
| 1 | 4.4 | 100.00% |
| 2 | 8.1 | 36.40% |
| 3 | 12.0 | 46.70% |
| 4 | 15.2 | 37.10% |
| 5 | 15.9 | 55.90% |
| 6 | 19.6 | 58.30% |
| 7 | 21.2 | 30.20% |
| 8 | 22.0 | 39.60% |
| 9 | 23.8 | 29.40% |
| 10 | 25.6 | 34.60% |

EXAMPLE 5

Sodium 4-[8-[(2-cyclopropyl-5-ethoxy-4-methyl-phenyl)methyl]-2-oxo-1,3,8-triazaspiro[4.5]decan-3-yl]-2-methoxy-benzoate

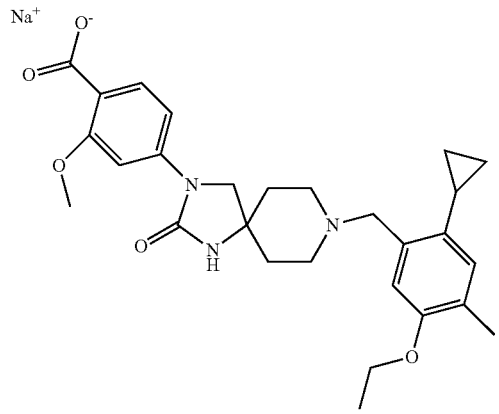 [SMILES: [Na+] ; CCOc1cc(CN2CCC3(CC2)CN(c2ccc(C(=O)[O-])c(OC)c2)C(=O)N3)c(C2CC2)cc1C]

Suspend methyl 4-[8-[(2-cyclopropyl-5-ethoxy-4-methyl-phenyl)methyl]-2-oxo-1,3,8-triazaspiro[4.5]decan-3-yl]-2-methoxy-benzoate (35 g, 68.95 mmol) in EtOH (550 mL) and add 1M aqueous NaOH (21 mL, 105 mmol). Heat the suspension to 70° C. for 1 hr; dilute with water (220 mL) to form a solution and stir to 70° C. for 30 min Distill the solution until a thin slurry is formed; dilute with EtOH (250 mL) and then distill down to a thick slurry. Dilute with EtOH (500 mL), stir at 22° C. for 60 min and filter. Dry the resulting solid under vacuum with a positive $N_2$ stream for 12 h to give 32.5 g of a white solid. Further dry the solid at 45° C. in a vacuum oven to constant weight (24 hrs) to give the title compound (32 g, 90% yield). ES/MS m/z 494.2 (M+H).

EXAMPLE 6

4-[8-[(2-Cyclopropyl-5-ethoxy-4-methyl-phenyl)methyl]-2-oxo-1,3,8-triazaspiro[4.5]decan-3-yl]-2-methoxy-benzoic acid

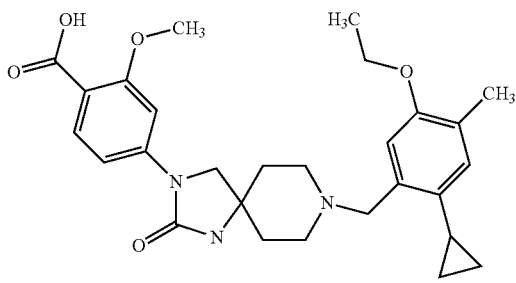 [SMILES: CCOc1cc(CN2CCC3(CC2)CN(c2ccc(C(=O)O)c(OC)c2)C(=O)N3)c(C2CC2)cc1C]

Suspend sodium 4-[8-[(2-cyclopropyl-5-ethoxy-4-methyl-phenyl)methyl]-2-oxo-1,3,8-triazaspiro[4.5]decan-3-yl]-2-methoxy-benzoate (470 mg, 0.91 mmol) in 6M citric acid buffer (9.4 mL) at 22° C., and stir for 2 hrs. Filter and dry the solid (10 mbar, 24° C., 18 hrs) to give the title compound as a white solid (378 mg, 84% yield). ES/MS m/z 494 (M+H).

EXAMPLE 7

4-[8-[(2-Cyclopropyl-5-ethoxy-4-methyl-phenyl)methyl]-2-oxo-1,3,8-triazaspiro[4.5]decan-3-yl]-2-methoxy-benzoic acid fumarate (1:1)

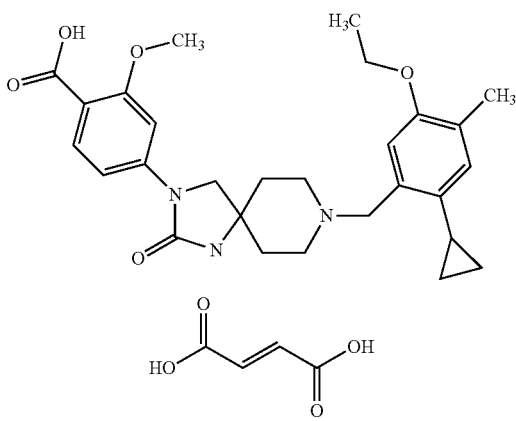

Add fumaric acid (40 mg, 0.324 mmol) as a solution in acetone (0.2 mL) to a slurry of 4-[8-[(2-cyclopropyl-5-ethoxy-4-methyl-phenyl)methyl]-2-oxo-1,3,8-triazaspiro[4.5]decan-3-yl]-2-methoxy-benzoic acid (132 mg, 0.267 mmol) in acetone (3 mL) at 55° C. Observe the formation of a solution that gives way to a white precipitate within about one minute. Stir the suspension for 1 h at 55° C. Allow the suspension to cool to rt with stirring. Collect the solid by vacuum filtration and air dry the solid in a fume hood to obtain the title compound.

EXAMPLE 8

4-[8-[(2-Cyclopropyl-5-ethoxy-4-methyl-phenyl)methyl]-2-oxo-1,3,8-triazaspiro[4.5]decan-3-yl]-2-methoxy-benzoic acid tosylate (1:1)

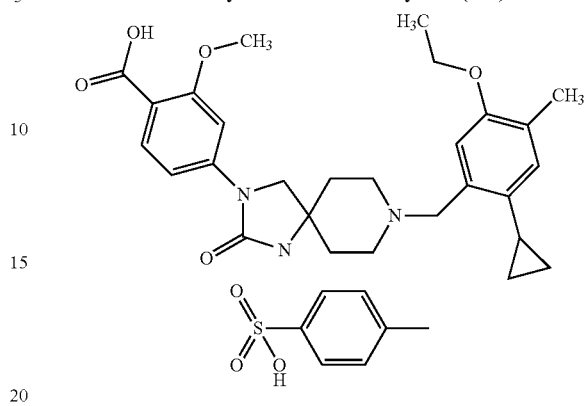

Add p-toluenesulfonic acid monohydrate (60 mg, 0.315 mmol) as a solution in acetone (0.2 mg) to a solution of 4-[8-[(2-cyclopropyl-5-ethoxy-4-methyl-phenyl)methyl]-2-oxo-1,3,8-triazaspiro[4.5]decan-3-yl]-2-methoxy-benzoic acid (150 mg, 0.304 mmol) in acetone (6 mL) at 55° C. Stir the solution for 2 h at 55° C. A white solid forms. Cool the suspension to rt and stir for 3 days. Collect the solid by vacuum filtration and air dry in a fume hood to obtain the title compound.

EXAMPLE 9

4-[8-[(5-Ethoxy-2-isopropyl-4-methyl-phenyl)methyl]-2-oxo-1,3,8-triazaspiro[4.5]decan-3-yl]-2-methoxy-benzoic acid

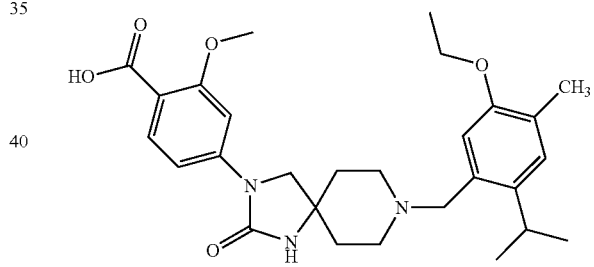

Add 2.5 M aqueous sodium hydroxide (0.3 mL, 0.74 mmol) followed by drops of EtOH to a solution of methyl 4-[8-[(5-ethoxy-2-isopropyl-4-methyl-phenyl)methyl]-2-oxo-1,3,8-triazaspiro[4.5]decan-3-yl]-2-methoxy-benzoate (180 mg, 0.353 mmol) in THF (1.2 mL). Stir the mixture at 60° C. overnight. Cool the mixture to room temperature and remove the solvents in vacuo. Dissolve the residue in DMSO and pour the mixture onto a HLB cartridge (6 g, Oasis) eluting with a gradient of 0 to 100% acetonitrile in aqueous (NH$_4$)HCO$_3$ (10 mM, pH 9). Collect the fractions containing the product and remove the solvent under vacuum. Subject the residue to reverse phase chromatography using a XBridge column (5 um, 19×100 mm) eluting with a gradient between 30 to 50% of B to A in 6 min at flow 25 mL/min (A: 20 mM ammonium bicarbonate pH=9, B: acetonitrile) to give the title compound as a white solid (138 mg, 79% yield). ES/MS m/z 496.3 (M+H).

EXAMPLES 10-16

The compounds of Examples 10-16 are prepared essentially as described in Example 9 using the corresponding ester as starting material.

TABLE 4

| Ex. No. | Structure | Chemical name | Yield (%) | ES/MS m/z |
|---|---|---|---|---|
| 10 | 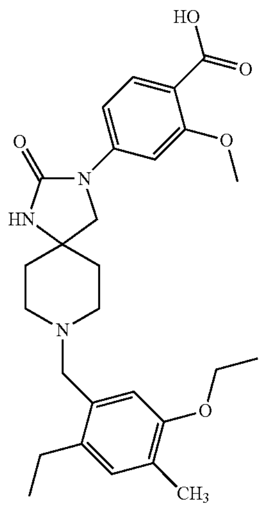 [SMILES: CCOc1cc(CN2CCC3(CC2)CN(c2ccc(C(=O)O)c(OC)c2)C(=O)N3)c(CC)cc1C] | 4-[8-[(5-Ethoxy-2-ethyl-4-methyl-phenyl)methyl]-2-oxo-1,3,8-triazaspiro[4.5]decan-3-yl]-2-methoxy-benzoic acid | 15 | 482.2 (M + H) |
| 11 | 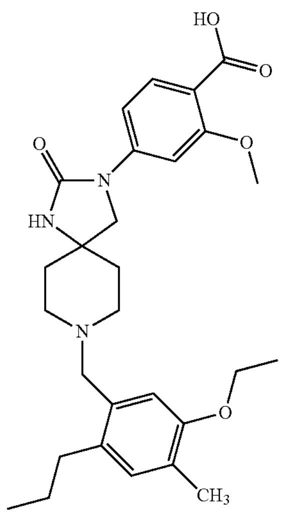 [SMILES: CCCc1cc(C)c(OCC)cc1CN1CCC2(CC1)CN(c1ccc(C(=O)O)c(OC)c1)C(=O)N2] | 4-[8-[(5-Ethoxy-4-methyl-2-propyl-phenyl)methyl]-2-oxo-1,3,8-triazaspiro[4.5]decan-3-yl]-2-methoxy-benzoic acid | 32 | 496.3 (M + H) |
| 12 | 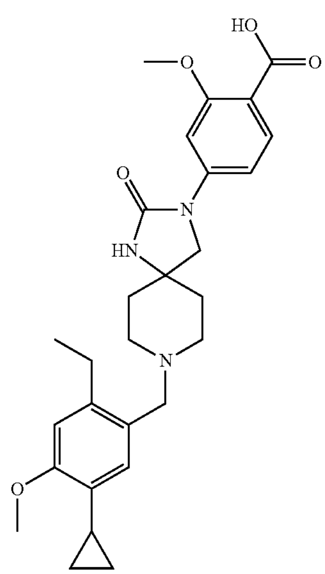 [SMILES: CCc1cc(OC)c(C2CC2)cc1CN1CCC2(CC1)CN(c1ccc(C(=O)O)c(OC)c1)C(=O)N2] | 4-[8-[(5-Cyclopropyl-2-ethyl-4-methoxy-phenyl)methyl]-2-oxo-1,3,8-triazaspiro[4.5]decan-3-yl]-2-methoxy-benzoic acid | 41 | 494.3 (M + H) |

TABLE 4-continued

| Ex. No. | Structure | Chemical name | Yield (%) | ES/MS m/z |
|---|---|---|---|---|
| 13 | 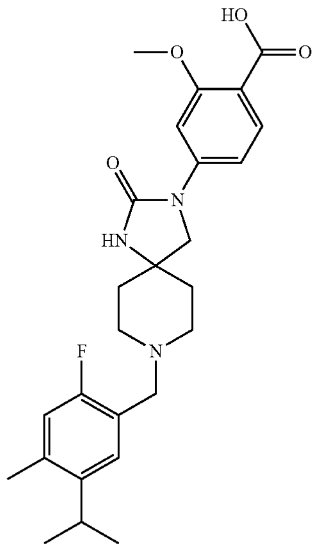 [SMILES: COc1cc(N2CC3(CCN(Cc4cc(C(C)C)c(C)cc4F)CC3)NC2=O)ccc1C(=O)O] | 4-[8-[(2-Fluoro-5-isopropyl-4-methyl-phenyl)methyl]-2-oxo-1,3,8-triazaspiro[4.5]decan-3-yl]-2-methoxy-benzoic acid | 42 | 470.2 (M + H) |
| 14 | 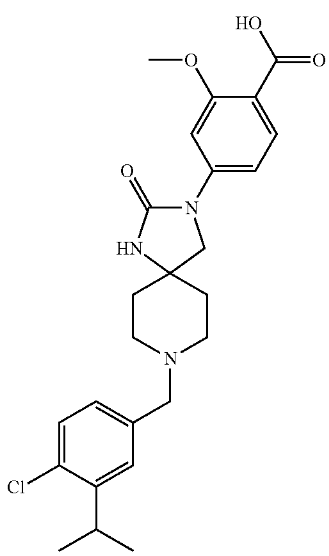 [SMILES: COc1cc(N2CC3(CCN(Cc4ccc(Cl)c(C(C)C)c4)CC3)NC2=O)ccc1C(=O)O] | 4-[8-[(4-Chloro-3-isopropyl-phenyl)methyl]-2-oxo-1,3,8-triazaspiro[4.5]decan-3-yl]-2-methoxy-benzoic acid | 91 | 472.2 (M + H) |

TABLE 4-continued

| Ex. No. | Structure | Chemical name | Yield (%) | ES/MS m/z |
|---|---|---|---|---|
| 15 | 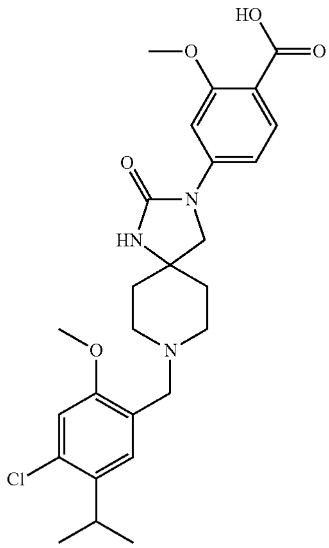 [SMILES: COc1cc(Cl)c(C(C)C)cc1CN1CCC2(CC1)CN(c1ccc(C(=O)O)c(OC)c1)C(=O)N2] | 4-[8-[(4-Chloro-5-isopropyl-2-methoxy-phenyl) methyl]-2-oxo-1,3,8-triazaspiro[4.5]decan-3-yl]-2-methoxy-benzoic acid | 24 | 502.2 (M + H) |
| 16 | 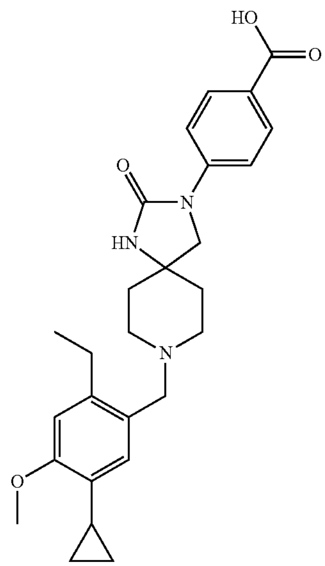 [SMILES: CCc1cc(OC)c(C2CC2)cc1CN1CCC2(CC1)CN(c1ccc(C(=O)O)cc1)C(=O)N2] | 4-[8-[(5-Cyclopropyl-2-ethyl-4-methoxy-phenyl)methyl]-2-oxo-1,3,8-triazaspiro[4.5]decan-3-yl]benzoic acid | 74 | 464.3 (M + H) |

EXAMPLE 17

4-[8-[(5-Ethoxy-2-isopropyl-4-methyl-phenyl)methyl]-2-oxo-1,3,8-triazaspiro[4.5]decan-3-yl]benzoic acid

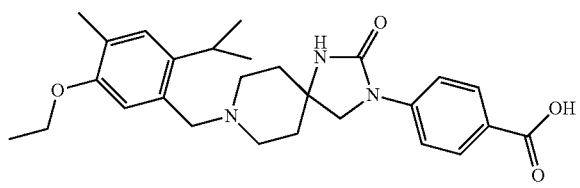 [SMILES: CCOc1cc(CN2CCC3(CC2)CN(c2ccc(C(=O)O)cc2)C(=O)N3)c(C(C)C)cc1C]

Add 4M HCl in 1,4-dioxane (4.3 mL) to a solution of tert-butyl 4-[8-[(5-ethoxy-2-isopropyl-4-methyl-phenyl)methyl]-2-oxo-1,3,8-triazaspiro[4.5]decan-3-yl]benzoate (0.45 g, 0.86 mmol) in DCM (17 mL). Stir the resulting mixture overnight at rt. Remove the solvent under reduced pressure. Dissolve the residue in DMSO and pour this mixture directly onto a HLB cartridge (6 g, Oasis) eluting with a gradient of 0 to 100% acetonitrile in aqueous (NH$_4$)HCO$_3$ (10 mM, pH 9) Collect the fractions containing the product and remove the solvent under vacuum. Subject the residue (370 mg) to reverse phase chromatography (XBridge C18 19×100 mm, 5 um) eluting with a gradient from 35 to 50% acetonitrile in aqueous (NH$_4$)HCO$_3$ (20 mM, pH 9) for 5 min at a flow rate of 25 mL/min, to give the title compound as a white solid (205 mg, 46% yield). ES/MS m/z 466 (M+H).

EXAMPLE 18 trans-4-[8-[(2-Cyclopropyl-5-ethoxy-4-methyl-phenyl)methyl]-2-oxo-1,3,8-triazaspiro[4.5]decan-3-yl]-1-methyl-cyclohexanecarboxylic acid

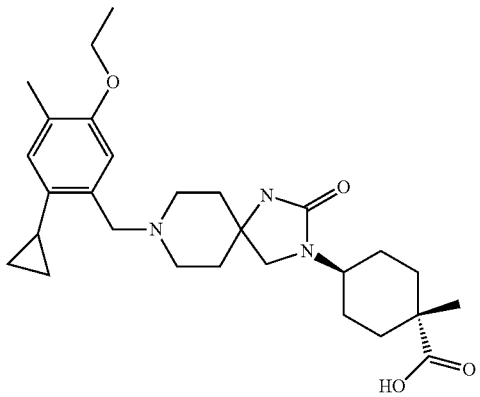 [SMILES: CCOc1cc(CN2CCC3(CC2)CN([C@H]2CC[C@](C)(C(=O)O)CC2)C(=O)N3)c(C2CC2)cc1C]

Add 1M aqueous NaOH (111 mL, 111 mmol) to a solution of trans-ethyl 4-[8-[(2-cyclopropyl-5-ethoxy-4-methyl-phenyl)methyl]-2-oxo-1,3,8-triazaspiro[4.5]decan-3-yl]-1-methyl-cyclohexanecarboxylate (28.5 g, 55.7 mmol) in THF (143 mL) and EtOH (57 mL). Heat the mixture to 80° C. and stir overnight (ca. 12 hrs). Cool the mixture to rt and adjust the pH to 6.4 with 35% aqueous HCl. Add a buffer solution (citric acid/sodium citrate, pH 7, 20 mL). Dilute the resulting slurry with water (400 mL) and stir for 15 min Filter to collect the solid. Dry the solid at 50° C. under reduced pressure for 2 days to give the title compound as a white solid (25.5 g, 95% yield). ES/MS m/z 484 (M+H).

EXAMPLE 19

Sodium trans-4-[8-[(5-ethoxy-4-methyl-2-propyl-phenyl)methyl]-2-oxo-1,3,8-triazaspiro[4.5]decan-3-yl]-1-methyl-cyclohexanecarboxylate

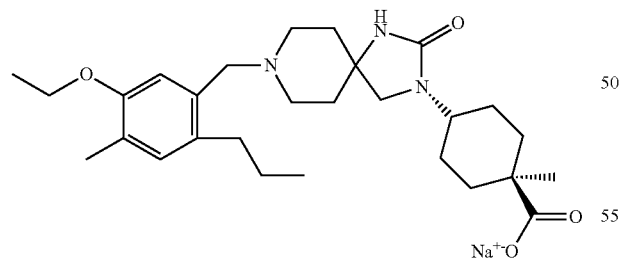

Suspend ethyl trans-4-[8-[(5-ethoxy-4-methyl-2-propyl-phenyl)methyl]-2-oxo-1,3,8-triazaspiro[4.5]decan-3-yl]-1-methyl-cyclohexanecarboxylate (30.9 g, 60.2 mmol) in EtOH (475 mL) and heat the suspension to 55° C.; then cool the mixture to 16° C. Add aqueous NaOH (10 mL, 50 w/w %, 189.4 mmol) to the suspension to induce an exotherm from 16 to 19.7° C. Heat the mixture to 75° C. for 8 hrs. Cool the mixture to 70° C. and stir an additional 12 hrs. Cool the mixture to 20° C. Filter to collect the solid and dry the solid at 40° C. under reduced pressure to give the title compound as an off-white solid (29.9 g, 98% yield). ES/MS m/z 486.4 (M+H).

EXAMPLE 20 trans-4-[8-[(5-Ethoxy-4-methyl-2-propyl-phenyl)methyl]-2-oxo-1,3,8-triazaspiro[4.5]decan-3-yl]-1-methyl-cyclohexanecarboxylic acid

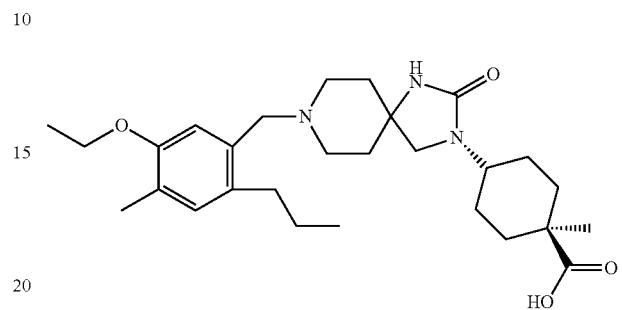

Dissolve ethyl trans-4-[8-[(5-ethoxy-4-methyl-2-propyl-phenyl)methyl]-2-oxo-1,3,8-triazaspiro[4.5]decan-3-yl]-1-methyl-cyclohexanecarboxylate (1.25 g, 2.4 mmol) in THF (8.1 mL) and add 1.2 N aqueous NaOH (10 mL, 12.17 mmol). Heat the mixture to 60° C. and stir for 16 hrs. Cool the mixture to room temperature and dilute it with chloroform/isopropanol (3/1). Add 1M aqueous HCl until pH=3. Separate the organic phase, dry over MgSO$_4$ and remove the solvent from the filtrate to provide a solid. Subject the solid to reverse phase flash chromatography (40 g Clarisep C-series C18 column, 20-35 um) eluting with 10 mM ammonium bicarbonate (A) and acetonitrile (B) using a gradient between 30% to 70% of B to A with a flow rate of 30 mL/min Collect the appropriate fractions and evaporate the solvents to give the title compound as a white solid (1.083 g, 88% yield). ES/MS m/z 486 (M+H).

EXAMPLE 21 trans-4-[8-[(5-Cyclopropyl-2-ethyl-4-methoxy-phenyl)methyl]-2-oxo-1,3,8-triazaspiro[4.5]decan-3-yl]-1-methyl-cyclohexanecarboxylic acid

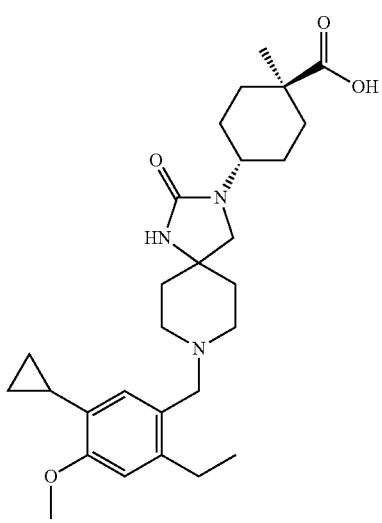 [SMILES: CCc1cc(OC)c(C2CC2)cc1CN1CCC2(CC1)CN([C@H]1CC[C@](C)(C(=O)O)CC1)C(=O)N2]

Prepare the title compound essentially by the method of Example 20 in 86% yield as a white solid starting from ethyl trans-4-[8-[(5-cyclopropyl-2-ethyl-4-methoxy-phenyl)methyl]-2-oxo-1,3,8-triazaspiro[4.5]decan-3-yl]-1-methyl-cyclohexanecarboxylate. ES/MS m/z 484.4 (M+H).

EXAMPLE 22 trans-4-[8-[(2-Cyclopropyl-5-ethoxy-4-methyl-phenyl)methyl]-2-oxo-1,3,8-triazaspiro[4.5]decan-3-yl]-1-ethyl-cyclohexanecarboxylic acid

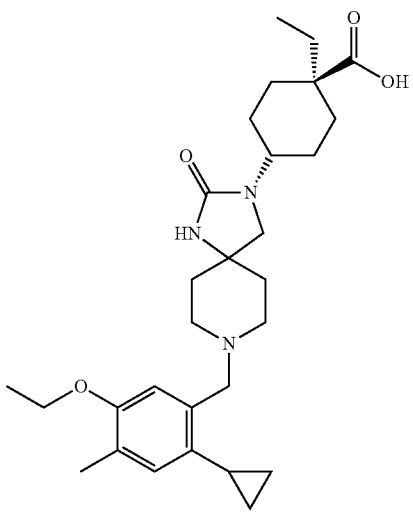

Add 5M aqueous NaOH (0.2 mL, 0.95 mmol) to a solution of ethyl trans-4-[8-[(2-cyclopropyl-5-ethoxy-4-methyl-phenyl)methyl]-2-oxo-1,3,8-triazaspiro[4.5]decan-3-yl]-1-ethyl-cyclohexanecarboxylate (0.1 g, 0.19 mmol) in THF (0.6 mL). Heat the mixture to 60° C. and stir for 18 hrs. Remove the solvent under reduced pressure. Dilute the residue with EtOAc and water. Adjust the pH to 3 with 1M aqueous HCl. Separate the organic phase. Dry the organic phase over MgSO$_4$; filter and remove the solvent from the filtrate under reduced pressure. Subject the residue to reverse phase chromatography (12 g Clarisep C-series C18 column, 20-35 um) eluting with 10 mM ammonium bicarbonate (A) and acetonitrile (B) using a gradient of 30% to 70% of B in A with a flow rate of 30 mL/min Collect the appropriate fractions and evaporate the solvent to give the title compound as a white solid (67 mg, 68% yield). ES/MS m/z 498 (M+H).

Biological Section

Somatostatin (SST) is a peptide hormone that is produced in pancreatic islets (5% of the bodies SST production) and the gut (65% of the bodies SST production). Of the five known SST receptors; SST receptor five (SSTR5) is highly expressed on the human β-cell (Braun, M., *Vitam. Horm.* (Chapter 7), Vol. 95, pg. 165-193, 2014). It is thought that SSTR5 is expressed on the enteroendocrine cells of the gut which are responsible for GLP-1 secretion (Hansen, L. et al., *Am. J. Physiol. Endocrinol. Metab.* 280, E1010-1018, 2000). SST itself is an inhibitor peptide hormone that has been shown to inhibit insulin (Braun, M.) and GLP-1 secretion (Hansen, L., 2000). Therefore, by selectively antagonizing SSTR5, the compounds of the present invention can increase insulin secretion directly from the β-cell and indirectly by increasing GLP-1 secretion from the gut.

Somatostatin Binding Assay

The antagonistic effect of the compound of Example 2 can be evaluated in human and mouse SSTR5 binding assays utilizing a scintillation proximity assay (SPA) format for a concentration response curve (CRC) ([$^{125}$I]-Somatostatin 14 binding to CHO-SSTR5 receptors). Perform measurement of SSTR5 binding utilizing either human somatostatin 5 membranes (manufactured by Perkin Elmer (ES-522-M400UA)) at a concentration of 0.4 μg/well or transiently expressed mouse SSTR5 membranes (generated in-house using Lipofectamine 2000 according to the manufacture's protocol (Life Technologies)) at a concentration of 8 μg/well. Homogenize membranes or dilute in buffer (prepare buffer from 25 mM HEPES (manufactured by HyClone), 5 mM MgCl$_2$ (manufactured by Sigma), 1 mM CaCl$_2$ (manufactured by Sigma), 0.5% BSA, pH 7.4 (manufactured by Gibco)). Prepare ligand solution with a final concentration of 0.25 nM ([$^{125}$I]-Somatostatin 14 (manufactured by Vitrax (VH31)). Use Wheat Germ Agglutinin (WGA) -PVT SPA beads (manufactured by Perkin Elmer (PRNQ0001)) at a concentration of 0.1 mg/well. Perform incubation for 1 hour at 22° C. with the following order of addition: compound (50 μl), ligand (50 μl), membranes (50 μl) and beads (50 μl) for a total volume of 200 μL. After one hour, spin the plates at 1000 rpm for six minutes before counting (Trilux counter). All the Examples listed herein exhibit human and mouse SSTR5 binding Ki less than 15 nM and 60 nM, respectively. The compound of Example 2 exhibits a human and mouse SSTR5 binding Ki of 0.54 nM and 4.87 nM, respectively.

β-Arrestin Functional Assay

A β-arrestin whole cell, functional assay, utilizing U2OS cells (human osteosarcoma cells), can directly measure effects of the compound of Example 2 on GPCR activity by determining its effects on the interaction of β-arrestin with the activated GPCR. Perform the CRC measurement of β-arrestin activity utilizing PathHunter CHO-K1 hSSTR5 β-arrestin cells from DiscoveRx (93-0402C2). Plate cells at a concentration of 5K/well in 50 μl of assay plating media in 384-well White Plates with opaque bottom (manufactured by Corning (3570)) and incubate overnight at 37° C./5% CO$_2$. Prepare test solutions by diluting 3 μl of Example 2 with 27 μl of DMSO for a step down dilution. Mix the diluted plate of the current invention on a plate shaker for five minutes. Wash cells with 50 μl of PBS (manufactured by HyClone) three times using a plate washer. After washing, use a Wellmate to add 15 μl of assay buffer (assay buffer prepared from HBSS (manufactured by HyClone), 20 mM HEPES (manufactured by HyClone) with 0.1% BSA (manufactured by Gibco)) to the cells followed by 100 nl of the present invention serial dilution. Incubate the cells at 37° C./5% CO$_2$ for 30 min. On a Multimek (Nanoscreen), add 5 μl of EC$_{80}$ agonist (37.5 nM SST14 (manufactured by Trocis (1157)) to cell plates. Incubate cells at 37° C./5% CO$_2$ for 90 min. On the Multimek (Nanoscreen), add 10 μl of PathHunter Detection Reagent working solution (manufactured by DiscoveRx (93-0001 L)) to each well. Incubate cells for 1 hour at room temperature and protect from light. After the hour incubation, read cells on an Envision 01 with chemiluminescence. Evaluation of the compound of Example 2 in this assay provides a β-arrestin IC$_{50}$ of 0.81 nM.

GLP-1 Secretion In Vivo

Use male c57BL/6 mice from Harlan Laboratories at 8-9 weeks of age to evaluate the effects of the compound of Example 2 on GLP-1 Secretion in vivo during a 12 hour pharmacokinetic/pharmacodynamic (PK/PD) study. Maintain mice under approved Animal Care and Use protocols for Lilly Research Laboratories and house on a 12 hour light cycle from 6 am to 6 pm. The day prior to the evaluation, fast the mice at 6 pm. The following day at 6 am, measure body weight and administer vehicle (HEC 1%/Tween 80 0.25%/Antifoam 0.05%) or the compound of Example 2 alone in vehicle (HEC 1%/Tween 80 0.25%/Antifoam 0.05% suspension). Collect blood samples for measurement of active GLP-1 levels and plasma exposure (~150 μl into EDTA coated Sarstedt Microvette® CB300 K2E tubes) at 0.25, 0.5, 1, 2, 4, 6, 9, 12 hours post-administration (only two samples collected from each mouse, euthanizing immediately following the second blood collection) Immediately after collecting the blood, preserve active GLP-1 samples with 5 μl of a mixture of DPP4 inhibitor (Bio Trend Cat. No. DPP-4)/aprotinin (Fisher BioReagents, Cat. No. BP250310), store on wet ice, spin down (3500 rpm, 4° C.). Draw off plasma, plate and freeze. Store GLP-1 samples at −80° C. until they can be analyzed utilizing a Meso Scale Discovery Active GLP-1 (v2) Kit (Cat. No. K150JWC-2). Calculate area under the curve (AUC) values. The results are listed below in Table 5. All data is indicated as mean±standard error and statistical analysis is indicated in Table 5 below. As demonstrated by the results, the compound of Example 2 has a non-glucose dependent effect to increase active GLP-1.

TABLE 5

|  | AUC (pg/mL-hour) (0-12 hours) | Fold Increase |
| --- | --- | --- |
| Vehicle | 32.1 ± 2.2 | 1.0 |
| Example 2: 0.3 mg/kg | 60.2 ± 2.9* | 1.9 |
| Example 2: 1 mg/kg | 71.2 ± 3.3* | 2.2 |
| Example 2: 3 mg/kg | 72.5 ± 4.3* | 2.3 |
| Example 2: 10 mg/kg | 87.3 ± 3.8* | 2.7 |
| Example 2: 30 mg/kg | 86.3 ± 4.6* | 2.7 |

Dunnett's Method vs Vehicle Control
*p < .001

Oral Glucose Tolerance Test (OGTT)

Use male c57BL/6 mice from Harlan Laboratories at 9-11 weeks of age to evaluate the effects of the compound of Example 1 on glucose lowering and GLP-1 secretion in vivo during an OGTT. Maintain mice under approved Animal Care and Use protocols for Lilly Research Laboratories and house on a 12 hour light cycle from 6 am to 6 pm. For the OGTT, fast the mice between 3 & 4 pm. The following day at 6 am, measure body weights and collect baseline blood samples via tail vein for glucose (Roche Aviva glucometer). Administer vehicle (HEC 1%/Tween 80 0.25%/Antifoam 0.05%), the compound of Example 1 alone in vehicle (HEC 1%/Tween 80 0.25%/Antifoam 0.05% suspension), a DPP-4 inhibitor (sitagliptin) alone in vehicle (HEC 1%/Tween 80 0.25%/Antifoam 0.05% solution) or a combination of the compound of Example 1 and sitagliptin orally 90 minutes prior to glucose administration. Just prior to glucose bolus (10 mL/kg, 3 g/kg, Sigma Cat. No. G7528) (0 min) and then at 15 min, 30 min and 60 min (post), collect blood samples for measurement of glucose (~3 μl) and for active GLP-1 levels (~40 μl into EDTA coated Sarstedt Microvette® CB300 K2E tubes) Immediately after collecting the blood, preserve active GLP-1 samples with 5 μl of a mixture of DPP-4 inhibitor (Bio Trend Cat. No. DPP-4)/aprotinin (Fisher BioReagents, Cat. No. BP250310), store on wet ice, spin down (3500 rpm, 4° C.), draw off plasma, plate and freeze. Store GLP-1 samples at −80° C. until they can be analyzed utilizing a Meso Scale Discovery Active GLP-1 (v2) Kit (Cat. No. K150JWC-2). Calculate area under the curve (AUC) values. The results are listed in Tables 6 and 7. All data is indicated as mean±standard error and statistical analysis is indicated in Tables 6 and 7. The data demonstrate that the compound of Example 1 has a glucose lowering effect and increased GLP-1 activity.

TABLE 6

| Glucose | AUC (mg/dl-min) (0-60 min) | % Lowering |
| --- | --- | --- |
| Vehicle | 9644 ± 794 | 0 |
| Example 1: 0.3 mg/kg | 7441 ± 612* | 23 |
| Example 1: 0.3 mg/kg/Sitagliptin: 10 mg/kg | 4300 ± 477** | 55 |
| Example 1: 30 mg/kg | 5674 ± 360** | 41 |
| Example 1: 30 mg/kg/Sitagliptin: 10 mg/kg | 3630 ± 142** | 62 |
| Sitagliptin: 10 mg/kg | 5308 ± 237** | 45 |

Dunnett's Method vs Vehicle Control
*p < 0.05,
**p < 0.001

TABLE 7

| Active GLP-1 | AUC (pg/mL-min) (0-60 min) | Fold Increase |
| --- | --- | --- |
| Vehicle | 51.7 ± 3.9 | 1 |
| Example 1: 0.3 mg/kg | 93.2 ± 15.5 | 1.8 |
| Example 1: 0.3 mg/kg/Sitagliptin: 10 mg/kg | 428 ± 36.1* | 8.3 |
| Example 1: 30 mg/kg | 151 ± 14.0 | 2.9 |
| Example 1: 30 mg/kg/Sitagliptin: 10 mg/kg | 1042 ± 194** | 20.2 |
| Sitagliptin: 10 mg/kg | 343 ± 73 | 6.6 |

Dunnett's Method vs Vehicle Control
*p < 0.05,
**p < 0.001

What is claimed is:

1. A compound of Formula 1:

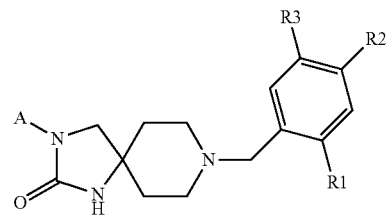

where A is selected from:

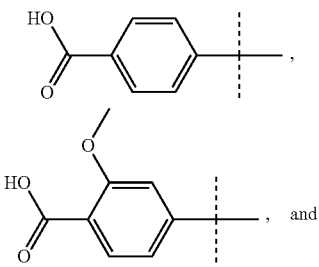

-continued

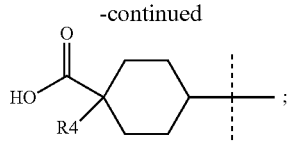

R1 is selected from: —$C_{1-3}$alkyl, F, Cl, —$OC_{1-2}$alkyl, and

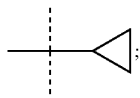

R2 is selected from: —$CH_3$, F, Cl, and —$OC_{1-2}$alkyl;
R3 is selected from: —$C_{1-3}$alkyl, —$OC_{1-2}$alkyl, and

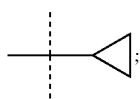

and
R4 is —$C_{1-2}$alkyl.

2. A compound according to claim 1 wherein A is

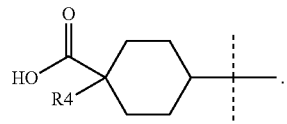

3. A compound according to claim 2 wherein the carboxylic acid group and the 2-oxo-1,3,8-triazaspiro[4.5]decan-3-yl group are trans to each other on the cyclohexane ring.

4. A compound according to claim 1 wherein R1 is selected from: —$CH_2CH_3$, —$CH_2CH_2CH_3$, and

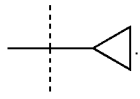

5. A compound according to claim 1 wherein R1 is F or —$OCH_3$.

6. A compound according to claim 1 wherein R2 is —$CH_3$.

7. A compound according to claim 2 wherein R4 is —$CH_3$.

8. A compound according to claim 1 wherein R1 is —$C_{1-3}$alkyl or

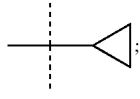

R2 is —$CH_3$; R3 is —$OCH_2CH_3$.

9. A compound of the Formula 2:

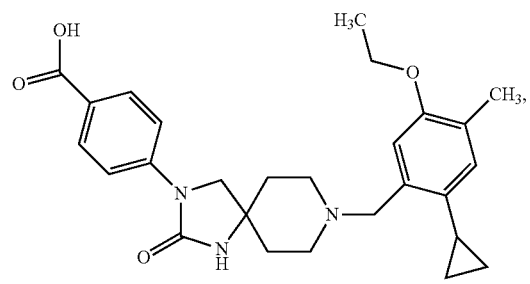

or a pharmaceutically acceptable salt thereof.

10. A compound according to claim 9 which is

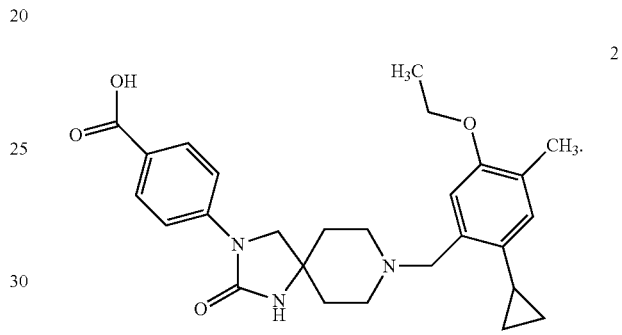

11. A compound which is sodium 4-[8-[(2-cyclopropyl-5-ethoxy-4-methyl-phenyl)methyl]-2-oxo-1,3,8-triazaspiro[4.5]decan-3-yl]benzoate.

12. A compound which is 4-[8-[(2-cyclopropyl-5-ethoxy-4-methyl-phenyl)methyl]-2-oxo-1,3,8-triazaspiro[4.5]decan-3-yl]benzoic acid tert-butyl amine.

13. A compound, which is sodium 4-[8-[(2-cyclopropyl-5-ethoxy-4-methyl-phenyl)methyl]-2-oxo-1,3,8-triazaspiro[4.5]decan-3-yl]benzoate in crystalline form characterized by an X-ray powder diffraction pattern obtained from a CuKα source ($\lambda$=1.54056 Å), which comprises peaks at:
  a) 4.4, 12.0, 15.6, and 19.6, +/−0.2° in 2θ; or
  b) 4.4, 12.0, 15.6, 15.9, 19.6, and 22.0+/−0.2° in 2θ; or
  c) 4.4, 8.1, 12.0, 15.6, 15.9, 19.6, 21.2, 22.0, and 25.6+/−0.2° in 2θ.

14. A compound which is 4-[8-[(2-cyclopropyl-5-ethoxy-4-methyl-phenyl)methyl]-2-oxo-1,3,8-triazaspiro[4.5]decan-3-yl]benzoic acid hydrate.

15. A compound which is:

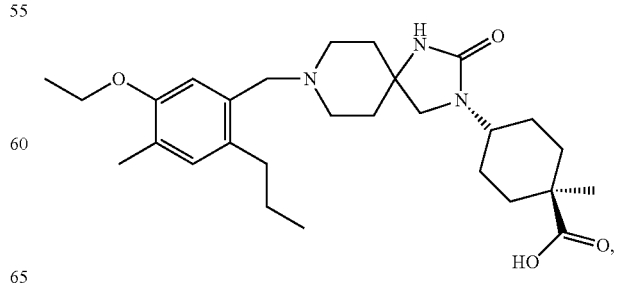

or a pharmaceutically acceptable salt thereof.

16. A compound which is:

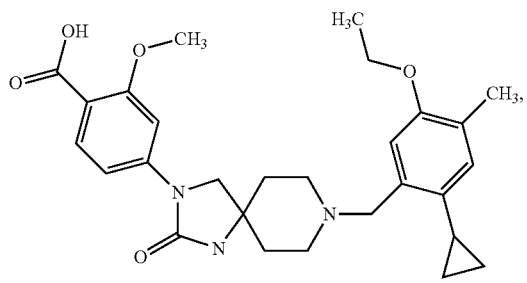 [SMILES: CCOc1cc(CN2CCC3(CC2)CN(c2ccc(C(=O)O)c(OC)c2)C(=O)N3)c(C2CC2)cc1C]

or a pharmaceutically acceptable salt thereof.

17. A pharmaceutical composition comprising greater than 80% w/w sodium 4-[8-[(2-cyclopropyl-5-ethoxy-4-methyl-phenyl)methyl]-2-oxo-1,3,8-triazaspiro[4.5]decan-3-yl]benzoate in crystalline form according to claim 13.

18. A pharmaceutical composition comprising greater than 95 w/w sodium 4-[8-[(2-cyclopropyl-5-ethoxy-4-methyl-phenyl)methyl]-2-oxo-1,3,8-triazaspiro[4.5]decan-3-yl]benzoate in crystalline form according to claim 13.

19. A method of treating a patient in need of treatment for diabetes comprising administering to the patient an effective amount of a compound, according to claim 9, or a pharmaceutically acceptable salt thereof.

20. A method according to claim 19 wherein diabetes is Type 2 diabetes mellitus.

21. A pharmaceutical composition comprising a compound according to claim 9 and at least one of a pharmaceutically acceptable carrier, diluent, or excipient.

22. A pharmaceutical composition comprising a compound according to claim 15 and at least one of a pharmaceutically acceptable carrier, diluent, or excipient.

23. A pharmaceutical composition comprising a compound according to claim 16 and at least one of a pharmaceutically acceptable carrier, diluent, or excipient.

24. A method of treating a patient in need of treatment for diabetes comprising administering to the patient an effective amount of a compound, according to claim 15, or a pharmaceutically acceptable salt thereof.

25. A method of treating a patient in need of treatment for diabetes comprising administering to the patient an effective amount of a compound, according to claim 16, or a pharmaceutically acceptable salt thereof.

* * * * *

UNITED STATES PATENT AND TRADEMARK OFFICE
CERTIFICATE OF CORRECTION

PATENT NO. : 9,920,056 B2  
APPLICATION NO. : 15/176222  
DATED : March 20, 2018  
INVENTOR(S) : Thomas James Beauchamp et al.

Page 1 of 1

It is certified that error appears in the above-identified patent and that said Letters Patent is hereby corrected as shown below:

On the Title Page

The title should read as follows:
2-OXO-1,3,8-TRIAZASPIRO[4.5][DECAN-3-YL] CARBOXYLIC ACID DERIVATIVES In the Claims In Column 59, Line 22, in Claim 18, after "95" insert --%.--

Signed and Sealed this
Twenty-sixth Day of June, 2018

Andrei Iancu
*Director of the United States Patent and Trademark Office*

UNITED STATES PATENT AND TRADEMARK OFFICE
CERTIFICATE OF CORRECTION

PATENT NO. : 9,920,056 B2
APPLICATION NO. : 15/176222
DATED : March 20, 2018
INVENTOR(S) : Thomas James Beauchamp et al.

It is certified that error appears in the above-identified patent and that said Letters Patent is hereby corrected as shown below:

On the Title Page

Item [54], Delete "2-OXO-1,3,8-TRIAZASPIRO[4.5]DECAN-3-YL] CARBOXYLIC ACID DERIVATIVES" and insert -- 2-OXO-1,3,8-TRIAZASPIRO[4.5]DECAN-3-YL CARBOXYLIC ACID DERIVATIVES --, therefor.

Item [56], Column 2 Line 1: Delete "Isoteric" and insert -- Isosteric --, therefor.

Item [56], Column 2 Line 4: Delete "non-petidic" and insert -- non-peptidic --, therefor.

Item [56], Column 2 Line 18: Delete "Endoctrinol" and insert -- Endocrinol --, therefor.

In the Specification

Column 1 Line 1: Delete "2-OXO-1,3,8-TRIAZASPIRO[4.5]DECAN-3-YL] CARBOXYLIC ACID DERIVATIVES" and insert -- 2-OXO-1,3,8-TRIAZASPIRO[4.5]DECAN-3-YL CARBOXYLIC ACID DERIVATIVES --, therefor.

Column 1 Line 4: Delete "2-OXO-1,3,8-TRIAZASPIRO[4.5]DECAN-3-YL] CARBOXYLIC ACID DERIVATIVES" and insert -- 2-OXO-1,3,8-TRIAZASPIRO[4.5]DECAN-3-YL CARBOXYLIC ACID DERIVATIVES --, therefor.

Signed and Sealed this
Twentieth Day of August, 2019

Andrei Iancu
*Director of the United States Patent and Trademark Office*